US009035044B2

(12) United States Patent
Nguyen et al.

(10) Patent No.: US 9,035,044 B2
(45) Date of Patent: May 19, 2015

(54) L-PROLINE AND CITRIC ACID CO-CRYSTALS OF (2S, 3R, 4R, 5S,6R)-2-(3-((5-(4-FLUOROPHENYL)THIOPEN-2-YL)METHYL)4-METHYLPHENYL)-6-(HYDROXYMETHYL)TETRAHYDRO-2H-PYRAN-3,4,5-TRIOL

(75) Inventors: Minh Nguyen, Dorchester Center, MA (US); Edwin A. Collier, Flemington, NJ (US)

(73) Assignee: Janssen Pharmaceutica NV, Beerse (BE)

( * ) Notice: Subject to any disclaimer, the term of this patent is extended or adjusted under 35 U.S.C. 154(b) by 203 days.

(21) Appl. No.: 13/466,249

(22) Filed: May 8, 2012

(65) Prior Publication Data

US 2012/0289694 A1     Nov. 15, 2012

Related U.S. Application Data

(60) Provisional application No. 61/483,887, filed on May 9, 2011.

(51) Int. Cl.
| | | |
|---|---|---|
| C07H 7/04 | (2006.01) | |
| C07D 409/10 | (2006.01) | |
| C07C 55/22 | (2006.01) | |
| C07D 207/16 | (2006.01) | |

(52) U.S. Cl.
CPC .............. *C07D 409/10* (2013.01); *C07C 55/22* (2013.01); *C07D 207/16* (2013.01)

(58) Field of Classification Search
CPC ....... C07H 7/04; C07D 207/16; C07C 59/265
USPC ........................................................ 536/122
See application file for complete search history.

(56) References Cited

U.S. PATENT DOCUMENTS

| | | | |
|---|---|---|---|
| 2,799,241 | A | 7/1949 | Wurster |
| 4,160,861 | A | 7/1979 | Cole et al. |
| 4,584,369 | A | 4/1986 | Klein et al. |
| 5,149,838 | A | 9/1992 | Humphrey et al. |
| 5,292,461 | A | 3/1994 | Juch et al. |
| 5,401,435 | A | 3/1995 | Burzio et al. |
| 5,424,406 | A | 6/1995 | Tsujihara et al. |
| 5,610,294 | A | 3/1997 | Lam et al. |
| 5,731,292 | A | 3/1998 | Tsujihara et al. |
| 5,767,094 | A | 6/1998 | Tsujihara et al. |
| 5,780,483 | A | 7/1998 | Widdowson et al. |
| 5,830,873 | A | 11/1998 | Tsujihara et al. |
| 5,861,385 | A | 1/1999 | Angerbauer et al. |
| 5,945,533 | A | 8/1999 | Kometani et al. |
| 6,048,842 | A | 4/2000 | Tsujihara et al. |
| 6,069,238 | A | 5/2000 | Hitchcock et al. |
| 6,153,632 | A | 11/2000 | Rieveley |
| 6,277,833 | B1 | 8/2001 | Angerbauer et al. |
| 6,297,363 | B1 | 10/2001 | Kubo et al. |
| 6,414,126 | B1 | 7/2002 | Ellsworth et al. |
| 6,420,513 | B2 | 7/2002 | Minami |
| 6,448,415 | B1 | 9/2002 | Lee et al. |
| 6,475,521 | B1 | 11/2002 | Timmins et al. |
| 6,515,117 | B2 | 2/2003 | Ellsworth et al. |
| 6,562,791 | B1 | 5/2003 | Maurya et al. |
| 6,617,313 | B1 | 9/2003 | Maurya et al. |
| 6,627,611 | B2 | 9/2003 | Tomiyama et al. |
| 6,800,761 | B1 | 10/2004 | Franc et al. |
| 7,008,959 | B2 | 3/2006 | Franc et al. |
| 7,045,665 | B2 | 5/2006 | Fujikura et al. |
| 7,074,826 | B2 | 7/2006 | Wechter et al. |
| 7,084,123 | B2 | 8/2006 | Fujikura et al. |
| 7,202,350 | B2 | 4/2007 | Imamura et al. |
| 7,271,153 | B2 | 9/2007 | Nishimura et al. |
| 7,288,528 | B2 | 10/2007 | Frick et al. |
| 7,294,618 | B2 | 11/2007 | Fushimi et al. |
| 7,375,213 | B2 | 5/2008 | Deshpande et al. |
| 7,417,032 | B2 | 8/2008 | Eckhardt et al. |
| 7,511,022 | B2 | 3/2009 | Beavers et al. |
| 7,566,699 | B2 | 7/2009 | Fushimi et al. |
| 7,576,064 | B2 | 8/2009 | Kikuchi et al. |
| 7,666,845 | B2 | 2/2010 | Cook et al. |
| 7,932,379 | B2 | 4/2011 | Deshpande et al. |
| 7,943,582 | B2 | 5/2011 | Nomura et al. |
| 7,943,788 | B2 | 5/2011 | Nomura et al. |
| 8,097,592 | B2 * | 1/2012 | Imamura et al. ................. 514/23 |
| 2001/0041674 | A1 | 11/2001 | Tomiyama et al. |
| 2002/0032164 | A1 | 3/2002 | Dale et al. |
| 2002/0052326 | A1 | 5/2002 | Washburn |
| 2002/0111315 | A1 | 8/2002 | Washburn et al. |
| 2003/0024914 | A1 | 2/2003 | Aleshin |
| 2003/0064935 | A1 | 4/2003 | Gougoutas |
| 2003/0087843 | A1 | 5/2003 | Washburn |
| 2003/0114390 | A1 | 6/2003 | Washburn et al. |
| 2003/0191121 | A1 | 10/2003 | Miller et al. |
| 2004/0053855 | A1 | 3/2004 | Fujikura et al. |
| 2004/0063646 | A1 | 4/2004 | Fujikura et al. |
| 2004/0110936 | A1 | 6/2004 | Ohsumi et al. |
| 2004/0116357 | A1 | 6/2004 | Fushimi et al. |
| 2004/0132669 | A1 | 7/2004 | Nishimura et al. |
| 2004/0138143 | A1 | 7/2004 | Glombik et al. |
| 2004/0259819 | A1 | 12/2004 | Frick et al. |

(Continued)

FOREIGN PATENT DOCUMENTS

| | | |
|---|---|---|
| CA | 2494177 A1 | 2/2004 |
| EP | 0355750 A1 | 2/1990 |

(Continued)

OTHER PUBLICATIONS

Viertelhaus, M. et al., Crystal Growth & Design, "Piracetam Co-Crystals with OH-Group Functionalized Carboxylic Acids", 2009, vol. 9, No. 5, pp. 2220-2228.*

Nomura et al., "Discovery of canagliflozin, a novel C-glucoside with thiophene ring, as sodium dependent glucose cotransporter 2 inhibitor for the treatment of type 2 diabetes mellitus.", Journal of Med. Chem., Sep. 9, 2012, pp. 6355-6360, vol. 53(17), American Chemical Society, US, XP007915324.

(Continued)

*Primary Examiner* — Layla Bland
*Assistant Examiner* — Bahar Craigo

(57) ABSTRACT

The present invention is directed to L-proline and citric acid co-crystals of (2S,3R,4R,5S,6R)-2-(3-((5-(4-fluorophenyl)thiophen-2-yl)methyl)-4-methylphenyl)-6-(hydroxymethyl)tetrahydro-2H-pyran-3,4,5-triol, pharmaceutical compositions containing said co-crystals and their use in the treatment glucose-related disorders such as Type 2 diabetes mellitus and Syndrome X.

6 Claims, 3 Drawing Sheets

(56) References Cited

U.S. PATENT DOCUMENTS

| | | |
|---|---|---|
| 2005/0014704 A1 | 1/2005 | Frick et al. |
| 2005/0032711 A1 | 2/2005 | Patel et al. |
| 2005/0032712 A1 | 2/2005 | Urbanski |
| 2005/0037980 A1 | 2/2005 | Rybczynski et al. |
| 2005/0037981 A1 | 2/2005 | Beavers et al. |
| 2005/0049203 A1 | 3/2005 | Nishimura et al. |
| 2005/0124555 A1 | 6/2005 | Tomiyama et al. |
| 2005/0124556 A1 | 6/2005 | Burton |
| 2005/0209166 A1 | 9/2005 | Eckhardt et al. |
| 2005/0233988 A1 | 10/2005 | Nomura et al. |
| 2005/0256317 A1 | 11/2005 | Sato et al. |
| 2006/0009400 A1 | 1/2006 | Eckhardt et al. |
| 2006/0035841 A1 | 2/2006 | Eckhardt et al. |
| 2006/0122126 A1 | 6/2006 | Imamura et al. |
| 2006/0189548 A1 | 8/2006 | Himmelsbach et al. |
| 2006/0217323 A1 | 9/2006 | Patel et al. |
| 2006/0229260 A1 | 10/2006 | Rybczynski et al. |
| 2006/0234954 A1 | 10/2006 | Urbanski |
| 2006/0247179 A1 | 11/2006 | Fushimi et al. |
| 2006/0258749 A1 | 11/2006 | Eckhardt et al. |
| 2006/0293251 A1 | 12/2006 | Urbanski et al. |
| 2007/0027092 A1 | 2/2007 | Himmelsbach et al. |
| 2007/0049537 A1 | 3/2007 | Eckhardt et al. |
| 2007/0060531 A1 | 3/2007 | Kikuchi et al. |
| 2007/0060545 A1 | 3/2007 | Nomura et al. |
| 2008/0027122 A1 | 1/2008 | Nomura et al. |
| 2008/0119422 A1 | 5/2008 | Nomura et al. |
| 2008/0132563 A1 | 6/2008 | Kakinuma et al. |
| 2008/0146515 A1* | 6/2008 | Nomura et al. ............... 514/23 |
| 2008/0234366 A1 | 9/2008 | Bindra et al. |
| 2009/0124702 A1 | 5/2009 | Siva Satya Krishna Babu et al. |
| 2009/0143316 A1* | 6/2009 | Imamura et al. ............... 514/25 |
| 2009/0233874 A1 | 9/2009 | Abdel-Magid et al. |
| 2010/0099883 A1 | 4/2010 | Fillers et al. |
| 2011/0009347 A1 | 1/2011 | Liang et al. |
| 2011/0087017 A1 | 4/2011 | Farina et al. |
| 2011/0212905 A1 | 9/2011 | Nomura et al. |
| 2012/0058941 A1 | 3/2012 | Nomura et al. |
| 2012/0115799 A1 | 5/2012 | Wang et al. |

FOREIGN PATENT DOCUMENTS

| | | |
|---|---|---|
| EP | 0348184 B1 | 3/1993 |
| EP | 0579204 A2 | 1/1994 |
| EP | 0579204 A3 | 1/1994 |
| EP | 0625513 B1 | 9/1999 |
| EP | 1172362 A1 | 1/2002 |
| EP | 1338603 A1 | 8/2003 |
| EP | 1528066 A1 | 5/2005 |
| EP | 1845095 | 10/2007 |
| EP | 1956023 A1 | 3/2008 |
| GB | 2359554 Q | 8/2001 |
| JP | 59039889 A | 3/1984 |
| JP | 63-233975 A | 9/1988 |
| JP | 4-253974 A | 9/1992 |
| JP | 06246354 A | 9/1994 |
| JP | 07242526 A | 9/1995 |
| JP | 9-263549 A | 10/1997 |
| JP | 2000-34230 A | 2/2000 |
| JP | 2000-34239 A | 2/2000 |
| JP | 2001-288178 A | 10/2001 |
| JP | 2002167430 A | 6/2002 |
| JP | 2003-12686 A1 | 1/2003 |
| JP | 2003238417 A | 8/2003 |
| JP | 2003313168 A | 11/2003 |
| WO | WO 93/09100 A1 | 5/1993 |
| WO | WO 93/21178 A1 | 10/1993 |
| WO | WO 94/14807 A1 | 7/1994 |
| WO | 96/13258 A1 | 5/1996 |
| WO | WO 97/17949 A1 | 5/1997 |
| WO | WO 97/25033 A1 | 7/1997 |
| WO | WO 98/42347 A1 | 10/1998 |
| WO | 99/67236 A | 12/1999 |
| WO | WO 99/67236 A | 12/1999 |
| WO | WO 00/27823 A1 | 5/2000 |
| WO | WO 00/28989 A1 | 5/2000 |
| WO | WO 00/74681 A1 | 12/2000 |
| WO | WO 01/27128 | 4/2001 |
| WO | WO 01/64669 A1 | 9/2001 |
| WO | WO 01/68660 A1 | 9/2001 |
| WO | WO 01/74834 A1 | 10/2001 |
| WO | WO 01/74835 A1 | 10/2001 |
| WO | WO 01/85167 A1 | 11/2001 |
| WO | WO 02/26706 A2 | 4/2002 |
| WO | WO 02/053573 A1 | 7/2002 |
| WO | WO 02/068439 A1 | 9/2002 |
| WO | WO 02/068440 A1 | 9/2002 |
| WO | WO 02/070020 A2 | 9/2002 |
| WO | WO 02/070020 A3 | 9/2002 |
| WO | WO 02/083066 A2 | 10/2002 |
| WO | WO 02/088157 A1 | 11/2002 |
| WO | WO 02/094262 A1 | 11/2002 |
| WO | WO 02/096357 A2 | 12/2002 |
| WO | WO 03/000712 A1 | 1/2003 |
| WO | WO 03/011880 A1 | 2/2003 |
| WO | WO 03/020737 A1 | 3/2003 |
| WO | WO 03/043621 A1 | 5/2003 |
| WO | WO 03/087104 A1 | 10/2003 |
| WO | WO 03/099836 A1 | 12/2003 |
| WO | WO 2004/007517 A1 | 1/2004 |
| WO | WO 2004/013118 A1 | 2/2004 |
| WO | WO 2004/014931 A1 | 2/2004 |
| WO | WO 2004/019958 A1 | 3/2004 |
| WO | WO 2004/052902 A1 | 6/2004 |
| WO | WO 2004/052903 A1 | 6/2004 |
| WO | WO 2004/063209 A2 | 7/2004 |
| WO | WO 2004/063209 A3 | 7/2004 |
| WO | WO 2004/064806 A | 8/2004 |
| WO | WO 2004/076470 A2 | 9/2004 |
| WO | WO 2004/080990 A1 | 9/2004 |
| WO | WO 2004/087727 A1 | 10/2004 |
| WO | WO 2004/099230 A1 | 11/2004 |
| WO | WO 2004/113359 A1 | 12/2004 |
| WO | WO 2005/009539 A2 | 2/2005 |
| WO | WO 2005/009954 A2 | 2/2005 |
| WO | WO 2005/012326 A1 | 2/2005 |
| WO | WO 2005/058845 A2 | 6/2005 |
| WO | WO 2006/010557 | 2/2006 |
| WO | 2006/080577 A1 | 8/2006 |
| WO | WO 2006/080577 A1 | 8/2006 |
| WO | WO 2006/108842 A1 | 10/2006 |
| WO | WO 2007/025943 A2 | 3/2007 |
| WO | WO 2007/031548 A2 | 3/2007 |
| WO | WO 2007/087441 A2 | 8/2007 |
| WO | 2007/114475 A1 | 10/2007 |
| WO | WO 2008/013322 A1 | 1/2008 |
| WO | 2008/020011 A1 | 2/2008 |
| WO | WO 2008/020011 A1 | 2/2008 |
| WO | WO 2008/034859 A1 | 3/2008 |
| WO | WO 2008/055870 A1 | 5/2008 |
| WO | WO 2008/055940 A2 | 5/2008 |
| WO | 2008/069327 A1 | 6/2008 |
| WO | WO 2008/070609 A1 | 6/2008 |
| WO | WO 2009/026537 A1 | 2/2009 |
| WO | WO 2009/035969 A1 | 3/2009 |
| WO | WO 2009/091082 A1 | 7/2009 |
| WO | WO 2009/121945 A2 | 10/2009 |
| WO | WO 2010/045656 A2 | 4/2010 |
| WO | WO 2010/092125 A1 | 8/2010 |

OTHER PUBLICATIONS

Vishweshwar et al., "Pharmaceutical co-crystals.", Journal of Pharmaceutical Sciences, Mar. 1, 2006, pp. 499-516, vol. 95(3), American Pharmaceutical Association, Washington, US, XP002443334.

Shultheiss et al., "Pharmaceutical Cocrystals and Their Physicochemical Properties.", Crystal Growth and Design, Jun. 3, 2009, pp. 2950-2967, vol. 9(6), XP55011939.

Shan et al., "The role of cocrystals in pharmaceutical science.", Drug Discovery Today, May 1, 2008, pp. 440-446, vol. 13(9-10), Elsevier, Rahway, NJ,US, XP022649919.

(56) References Cited

OTHER PUBLICATIONS

Beck-Nielsen et al., "In Vivo Glucose Metabolism, Insulin Secretion, and Insulin Action in Europids with Non-Insulin Dependent Diabetes Mellitus (NIDDM) and Their First-Degree Relatives.", *Diabet. Med.,* Sep. 1996, pp. S78-S84, vol. 13, Suppl 6.
Caumo et al., "Insulin Sensitivity from Meal Tolerance Tests in Normal Subjects: A Minimal Model Index.", *J. Clin. Endocrinol. Metab.,* 2000, pp. 4396-4402, vol. 85(11).
Dinneen, S.F., "The Postprandial State: Mechanisms of Glucose Intolerance.", *Diabet. Med.,* Aug. 1997, pp. S19-S24, vol. 14, Suppl 3.
Emancipator K., "Laboratory Diagnosis and Monitoring of Diabetes Mellitus.", *Am. J. Clin. Pathol.,* Nov. 1999, pp. 665-674, vol. 112(5).
Goldberg, R.B., "Prevention of Type 2 Diabetes.", *Med. Clin. North. Am.,* Jul. 1998, pp. 805-821, vol. 82(4).
Groop et al., "Characterization of the Prediabetic State.", *Am. J. Hypertens.,* Sep. 1997, pp. 172S-180S, vol. 10(9, Pt.2).
Haffner, S.M., "Impaired Glucose Tolerance, Insulin Resistance and Cardiovascular Disease.", *Diabet. Med.,* Aug. 1997, pp. S12-S18, vol. 14, Suppl 3.
Haffner, S.M., "The Prediabetic Problem: Development on Non-Insulin Dependent Diabetes Mellitus and Related *J Diabetes Complications.*", Mar.-Apr. 1997, pp. 69-76, vol. 11(2).
Ramlo-Halsted et al., "The Natural History of Type 2 Diabetes.", *Prim. Care.,* Dec. 1999, pp. 771-789, vol. 26(4).
Written Opinion of the International Searching Authority relating to International Patent Application No. PCT/US2012/037062. Date of Mailing of Written Opinion: Aug. 8, 2012.
Adachi et al., "T-1095, a Renal $Na^+$-Glucose Transporter Inhibitor, Improves Hyperglycemia in Streptozotocin-Induced Diabetic Rats.", *Metabolism,* Aug. 2000, pp. 990-995, vol. 49(8).
Ahmad et al., "Synthesis and Structure Determination of Some Oxadiazole-2-Thione and Triazole-3-Thione Galactosides.", *Nucleosides, Nucleotides & Nucleic Acids,* 2001, pp. 1671-1682, vol. 20(9).
Albertoni Borghese et al., "Inhibitors of sodium/glucose cotransport.", *Drugs of the Future,* Apr. 2009, pp. 297-305, vol. 34(4), Prous Science, XP007915342.
Amishiro et al., "Synthesis and Antitumor Activity of Duocarmycin Derivatives: A-Ring Pyrrole Compounds Bearing 5-Membered Heteroarylacryloyl Groups.", *Chem. Pharm. Bull.,* Oct. 1999, pp. 1393-1403, vol. 47(10).
Appleton et al., "A Mild and Selective C-3 Reductive Alkylation of Indoles." *Tetrahedron Letters,* 1993, pp. 1529-1532, vol. 34(9).
Apsel et al., "General Entries to C-aryl glycosides. Formal synthesis of galtamycinone.", *Tetrahedron Letters,* 2003, pp. 1075-1077, vol. 44.
Arakawa et al., "Improved diabetic syndrome in C57BL/KsJ-db/db Mice by Oral Administration of the Na+-Glucose Cotransporter Inhibitor T-1095.", *British Journal of Pharmacology,* 2001, pp. 578-586, vol. 132.
Banker, Modern Pharmaceutics, Third Edition, Marcel Dekker, Inc., published 1996, p. 596.
Benhaddou et al.,"Tetra-n-propylammonium tetra-oxoruthenate(VII): a reagent of choice for the oxidation of diversely protected glycopyranoses and glycofuranoses to lactones.", *Carbohydrate Research,* 1994, pp. 243-250, vol. 260.
Bertolini et al., "A New Simple One-Pot Regioselective Preparation of Mixed Diesters of Carbonic Acid.", *Journal of Organic Chemistry,* 1998, pp. 6031-6034, vol. 63(17).
Blair et al., "Effect of Ring Fluorination on the Pharmacology of Hallucinogenic Tryptamines.", *J. Med. Chem.,* 2000, pp. 4701-4710, vol. 43.
Boehm et al., "Novel Inhibitors of DNA Gyrase: 3D Structure Based Biased Needle Screening, Hit Validation by Biophysical Methods, and 3D Guided Optimization. A Promising Alternative to Random Screening.", *J. Med. Chem.,* 2000, pp. 2664-2674, vol. 43(14).
Bookser, B.C., "2-Benzyloxymethyl-5-(tributylstannyptetrazole. A reagent for the preparation of 5-aryl-and 5-heteroaryl-1H-tetrazoles via the Stille reaction." *Tetrahedron Letters,* 2000, pp. 2805-2809, vol. 41.
Bouillon et al., "Synthesis of novel halopyridinylboronic acids and esters. Part 2: 2,4, or 5-Halopyridin-3-yl-boronic acids and esters.", *Tetrahedron,* 2002, pp. 3323-3328, vol. 58.
Bouillon et al., "Synthesis of novel halopyridinylboronic acids and esters. Part 3: 2, or 3-Halopyridin-4-yl-boronic acids and esters.", *Tetrahedron,* 2002, pp. 4369-4373, vol. 58.
Bouillon et al., "Synthesis of novel halopyridinylboronic acids and esters. Part 4: Halopyridin-2-yl-boronic acids and esters are stable, crystalline partners for classical Suzuki cross-coupling.", *Tetrahedron,* 2003, pp. 10043-10049, vol. 59.
Braga et al., "Making crystals from crystals: a green route to crystal engineering and polymorphism.", Chem. Commun., 2005, pp. 3635-3645.
Brooks et al., "Boron Trichloride/Tetra-n-Butylammonium Iodide: A Mild, Selective Combination Reagent for the Cleavage of Primary Alkyl Aryl Ethers.", *J. Org. Chem.,* 1999, pp. 9719-9721, vol. 64.
Byrn et al., "Pharmaceutical Solids: A Strategic Approach to Regulatory Considerations.", *Pharml. Res.,* 1995, pp. 945-954, vol. 12(7).
CAS Reg. No. 487001-40-1, IPOrganisers, Entered STN Feb. 7, 2003, pp. 1-2.
Cicchillo et al., "A convenient synthesis of glycosyl chlorides from sugar hemiacetals using triphosgene as the chlorine source.", Carbohydrate Research, 2000, pp. 431-434, vol. 328.
Clayden et al., "Dearomatizing Cyclization of Arylsulfonylalkoxymethyl Lithiums: A Route to the Podophyllotoxin Skeleton.", *Organic Letters,* 2003, pp. 831-834, vol. 5(6).
Comins et al., "Synthesis of 3-Substituted Indoles Via N-Acylindolium Ions.", *Tetrahedron Letters,* 1986, pp. 1869-1872, vol. 27(17).
Cottet et al., "Recommendable Routes to Trifluoromethyl-Substituted Pyridine—and Quinolinecarboxylic Acids.", *Eur. J. Org. Chem.,* 2003, pp. 1559-1568.
Czernecki et al., "C-Glycosides. 7. Stereospecific C-Glycosylation of Aromatic and Heterocyclic Rings.", *J. Org. Chem.,* 1989, pp. 610-612, vol. 54.
De Las Heras et al., "Alkylating Nucleosides 1. Synthesis and Cytostatic Activity of N-Glycosyl(halomethyl)-1,2,3-triazoles. A New Type of Alkylating Agent.", *Journal of Medicinal Chemistry,* 1979,pp. 496-501, vol. 22(5).
Deeg et al., "Pioglitazone and Rosiglitazone Have Different Effects on Serum Lipoprotein Particle Concentrations and Sizes in Patients With Type 2 Diabetes and Dyslipidemia.", *Diabetes Care,* Oct. 2007, pp. 2458-2464, vol. 30(10).
Deetjen et al., "Renal Handling of D-Glucose and Other Sugars.", *Textbook of Nephrology,* 3rd Edition, 1995, pp. 90-94. vol. 1.
Devivar et al., "Benzimidazole Ribonucleosides: Design, Synthesis, and Antiviral Activity of Certain 2-(Alkylthio)- and 2-(Benzylthio)-5,6-dichloro-1-(.beta.-D-ribofuranosyl)benzimidazolesl.", *J.Med. Chem.,* 1994, pp. 2942-2949, vol. 37.
Dewynter et al., "Synthesis of Pseudomucleosides containing Chiral Sulfahydantoins as Aglycone (II).", *Tetrahedron,* 1996, pp. 993-1004, vol. 52(3).
Dillard et al., "Indole Inhibitors of Human Nonpancreatic Secretory Phospholipase A2. 1. Indole-3-acetamides.", *J. Med. Chem.,* 1996, pp. 5119-5136, vol. 39.
Dondoni et al., "Stereoselective synthesis of C-glycosylphosphonates from their ketols. Reconsideration of an abandoned route.", *Tetrahedron: Asymmetry,* 2000, pp. 305-317, vol. 11.
Dondoni et al., "Thiazole-Based Synthesis of Formyl C-Glycosides.", *J. Org. Chem.* 1994, pp. 6404-6412, vol. 59.
Dudash et al., "Glycosylated dihydrochalcones as potent and selective sodium glucose co-transporter 2 (SGLT2) inhibitors," *Bioorganic & Medicinal Chemistry Letters,* 2004, pp. 5121-2125, vol. 14.
Dunn et al., "Analgetic and antiinflammatory 7-Aroylbenzofuran-5-ylacetic acids and 7-Aroylbenzothiophene-5-ylacetic Acids.", *Journal of Med. Chem.,* 1986, pp. 2326-2329, vol. 29(1).

(56) References Cited

OTHER PUBLICATIONS

Eid et al., "Reaction of Some 1,2,4-Triazines with Acetobromoglucose", *Arch. Pharm.* (Weinheim), 1990, pp. 243-245, vol. 323.

Ellsworth et al., "Aglycone exploration of C-arylglucoside inhibitors of renal sodium-dependent glucose transporter SGLT2.", *Bioorganic & Medicinal Chemistry Letters*, 2008, pp. 4770-4773, vol. 18.

Ellsworth et al., "C-Arylglucoside synthesis: triisopropylsilane as a selective reagent for the reduction of an anomeric C-phenyl ketal.", *Tetrahedron: Asymmetry*, 2003, pp. 3243-.3247, vol. 14.

Frahn et al., "Functionalized AB-Type Monomers for Suzuki Polycondensation.", *Synthesis*, Nov. 1997, pp. 1301-1304.

Fresneda et al., "Synthesis of the indole alkaloids meridianins from the tunicate *Aplidium meridianum*,", *Tetrahedron* 2001, pp. 2355-2363, vol. 57.

Fuller et al., "Thienothiophenes. Part 2. Synthesis, metallation and bromine-lithium exchange reactions of thieno[3,2-b-thiophene and its polybromo derivatives.", *J. Chem. Soc.*, Perkin Trans. 1., 1997, pp. 3465-3470.

Ganesh et al., "Synthesis and biological evaluation of fluorescently labeled epothilone analogs for tubulin binding studies.", *Tetrahedron*, 2003, pp. 9979-9984, vol. 59.

Gershell, L., "Type 2 diabetes market", *Nature Reviews Drug Discovery*, May 2005, pp. 367-368, vol. 4.

Gohier et al., "Ortho-Metalation of Unprotected 3-Bromo and 3-Chlorobenzoic Acids with Hindered Lithium Dialkylamides.", *J. Org. Chem.*, 2003, pp. 2030-2033, vol. 68.

Gong, H., et al., "Diastereoselective Ni-Catalyzed negishi Cross Coupling Approach to Saturated, Fully Oxygenated C-Alkyl and C-Aryl Glycosides." *Journal of the American Chemical Society*, Sep. 10, 2008, pp. 12177-12183, vol. 130(36), XP002612364.

*Goodman & Gilman's The Pharmacological Basis of Therapeutics*, 10th Edition, McGraw-Hill Medical Publishing Division, 2001, pp. 54-57.

Greene et al., *"Protective Groups in Organic Synthesis."*, 3rd Edition, 1999, pp. 116-121.

Greene et al., *"Protective Groups in Organic Synthesis."*, 3rd Edition, 1999, pp. 170.

Gronowitz et al., "Some Substitution Reactions of 1-(2-Thienyl)pyrazole and 1-(3'-Thienyl)pyrazole.", *Chemica Scripta.*, 1979, pp. 157-161, vol. 13.

Gros et al., "Efficient and Regioselective Access to Bis-heterocycles via Palladium-Catalysed Coupling of Organostannanes and Organozincates Derived from C-6 Lithiated 2-Methoxypyridine.", *Synthesis*, 1999, pp. 754-756, No. 5.

Han et al., "Dapagliflozin, a Selective SGLT2 Inhibitor, Improves Glucose Homeostasis in Normal and Diabetic Rats.", *Diabetes*, Jun. 2008, pp. 1723-1729, vol. 57, New York.

Handlon, A. L., "Sodium glucose co-transporter 2 (SGLT2) inhibitors as potential antidiabetic agents.", *Expert Opin. Ther. Patents*, 2005, pp. 1531-1540, vol. 15(11).

Hixon et al., "Sizing Materials by Crushing and Grinding.", *Chemical Engineer*, Nov. 1990, pp. 94-103.

Hofslokken et al., "Convenient Method for the ortho-Formylation of Phenols.", Acta Chemica Scandinavica, 1999, pp. 258-262, vol. 53.

Hongu et al., "Na$^+$-Glucose Cotransporter Inhibitors as Antidiabetic Agents. II.[1]) Synthesis and Structure—Activity Relationships of 4'-Dehydroxyphlorizin Derivatives.", *Chem. Pharm. Bull.*, 1998, pp. 22-33, vol. 46(1).

Horton et al., "Synthetic Routes to Higher-Carbon Sugars. Reaction of Lactones with 2-Lithio-1,3-Dithiane.", *Carbohydrate Research*, 1981, pp. 27-41, vol. 94.

Hu et al., "A New Approach Towards the Yellowing Inhibition of Mechanical Pulps. Part I: Selective Removal of alpha-Hydroxyl and alpha-Carbonyl Groups in Lignin Model Compounds.", *Holzforschung*, 1999, pp. 43-48, vol. 53(1).

Huang-Minlon, "Reduction of Steroid Ketones and other Carbonyl Compounds by Modified Wolff-Kishner Method.", *J. Am. Chem. Soc.*, Oct. 1949, pp. 3301-3303, vol. 71.

Ibrahim et al., "Facile Approach for the Selective Glycodisation of Cyclic Asymmetric Amides and Thioamides.", *Carbohydrate Letters*, 1996, pp. 425-432, vol. 1.

Ibrahim et al., "Selective Synthesis and Structure of 2-N- and 3-S-Glucosyl-1,2,4-Triazoles of Potential Biological Interest.", *Carbohydrate Letters*, 1999, pp. 331-338, vol. 3(5).

Idris et al., "Sodium-glucose co-transporter-2 inhibitors: an emerging new class of oral antidiabetic drug.", *Diabetes, Obesity and Metabolism*, 2009, pp. 79-88, vol. 11(2), GB, XP007915350.

Isaji, M., "Sodium-glucose cotransporter inhibitor for diabetes.", *Current Opinion in Investigational Drugs*, 2007, pp. 285-292, vol. 8(4).

Jain et al., "Polymorphism in Pharmacy.", *Indian Drugs*, 1986, pp. 315-329, vol. 23(6).

Kaelin et al., "General Strategies for the Synthesis of the Major Classes of C-aryl Glycosides.", *J. Am. Chem. Soc.*, 2001, pp. 6937-6938, vol. 123.

Kahn et al., "Normalization of Blood Glucose in Diabetic Rats with Phlorizin Treatment Reverses Insulin-resistant Glucose Transport in Adipose Cells without Restoring Glucose Transporter Gene Expression.", *Journal of Clinical Investigation*, 1991, pp. 561-570, vol. 87.

Kanai et al., "The Human Kidney Low Affinity Na+/Glucose Cotransporter SGLT2: Delineation of the Major Renal Reabsorptive Mechanism for D-Glucose.", *J. Clin. Invest.*, Jan. 1994, pp. 397-404, vol. 93.

Kasahara et al., "A missense mutation in the Na+/glucose cotransporter gene SGLT1 in a patient with congenital glucose-galactose malabsorption: normal trafficking but inactivation of the mutant protein.", *Biochimica et Biophysics Acta* 2001, pp. 141-147, vol. 1536.

Katz et al., "Quantitative Insulin Sensitivity Check Index: A Simple, Accurate Method for Assessing Insulin Sensitivity in Humans.", *J. Of Clin. Endocrinology & Metabolism*, 2000, pp. 2040-2410, vol. 85(7).

Ketcha et al., "Synthesis of Alyl-Substituted N-Protected Indoles via Acylation and Reductive Deoxygenation1.", *J. Org. Chem.*, 1989, pp. 4350-4356, vol. 54.

Khan et al, "Reactions of Phenyl-Substituted Heterocyclic Compounds—II. Nitrations and Brominations of 1-Phenylpyrazole Derivatives.", *Canadian Journal of Chemistry*, 1963, pp. 1540-1547, vol. 41.

Kitagawa, K., et al., "Halogen—Magnesium Exchange via Trialkylmagnesates for the Preparation of Aryl- and Alkenylmagnesium Reagents.", *Angew. Chem. Int. Ed.*, 2000, pp. 2481-2493, vol. 39(14).

Klapars et al., "Copper-Catalyzed Halogen Exchange in Aryl Halides: An Aromatic Finkelstein Reaction.", *J. Am. Chem. Soc.*, 2002, pp. 14844-14845, vol. 124(50).

Knochel, P., et al., *Organic Reactions*, vol. 58, Chapter 2: Preparation and Application of Functionalized Organozinc Compounds by., pp. 417-490, Edited by L. E. Overman, et al., John Wiley &Sons, Inc., Publishers, 2001.

Lee et al., "Recent Advances in Aryl C-Glycoside Synthesis.", *Current Topics in Medicinal Chemistry*, 2005, pp. 1333-1350, vol. 5.

Lee et al., "Synthesis and in Vitro Activity of Novel Isoxazolyl Tetrahydropyridinyl Oxazolidinone Antibacterial Agents.", *Bioorganic & Medicinal Chemistry Letters*, 2003, pp. 4117-4120, vol. 13.

Lieberman et al., *"Pharmaceutical Dosage Forms"*, Second Edition, 1990, Marcel Dekker pp. 462-472, vol. 2.

Lin et al., "Syntheses of Guanidinoglycosides with the Inventive use of Mitsunobu Conditions and 1, 8-Diazabicyclo[5.4.0]undec-7-ene.", *Synthesis*, 2003, pp. 255-261, No. 2.

Link et al., "A method for preparing C-glycosides related to phlorizin.", *Tetrahedron Letters*, 2000, pp. 9213-9217, vol. 41.

Lipscombe et al., "Trends in diabetes prevalence, incidence, and mortality in Ontario, Canada 1995-2005: a population-based study.", *Lancet*, 2007, vol. 369, pp. 750-756.

Maatooq et al., "C-*p*-Hydroxybenzoylglycoflavones From *Citrullus colocynthis.*", *Phytochemistry*, Jan. 1997, pp. 187-190, vol. 44(1).

(56) References Cited

OTHER PUBLICATIONS

Mackenzie et al., "Biophysical Characteristics of the Pig Kidney Na+/Glucose Cotransporter SGLT2 Reveal a Common Mechanism for SGLT1 and SGLT2.", *J. Biol. Chem.*, 1996, vol. 271, pp. 32678-32683, No. 5.
Manis et al., "Metabolism of 4,4'-Methylenebis(2-chloroaniline) by Canine Liver and Kidney Slices.", *Drug Metabolism and Disposition*, 1986, pp. 166-174, vol. 14(2).
Marsenic, O. Md, "Glucose Control by the Kidney: An Emerging Target in Diabetes." *Am. J. of Kidney Diseases*, May 2009, pp. 875-883, vol. 53(5).
Martin, S. F., "Unified Strategy for the Synthesis of C-aryl glycosides*.", *Pure Appl. Chem.*, 2003, pp. 63-70, vol. 75(1).
Matsuda et al., "Insulin Sensitivity Indices Obtained From Oral Glucose Tolerance Testing: Comparison with the euglycemic insulin clamp.", *Diabetes Care*, Sep. 1999, pp. 1462-1470, vol. 22(9).
Matthews et al., "Homeostasis model assessment: insulin resistance and --cell function from fasting plasma glucose and insulin concentrations in man.", *Diabetolgia*, 1985, pp. 412-419, vol. 28.
Meanwell et al., "Regiospecific Functionalization of 1,3-Dihydro-2H-benzimidazol-2-one and Structurally Related Cyclic Urea Derivates.", *J. Org. Chemistry* 1995, pp. 1565-1582, vol. 60(6).
Meng et al., "Discovery of Dapagliflozin: a Potent, Selective Renal Sodium-Dependent Glucose Cotransporter 2 (SGLT2) Inhibitor for the Treatment of Type 2 Diabetes.", *J. Med. Chem.*, 2008, pp. 1145-149, vol. 51(5).
Messaoudi et al, "Synthesis and biological evaluation of oxindoles and benzimidazolinones derivatives," European Journal of Medicinal Chemistry, 2004, pp. 453-458, vol. 39.
Mewshaw et al., "New Generation Dopaminergic Agents. 7. Heterocyclic Bioisosteres that Exploit the 3-Oh-Phenoxyethylamine D2 Template", Bioorganic & Medicinal Chemistry Letters, 1999, pp. 2593-2598, vol. 9.
Miyaura et al., "Palladium-Catalyzed Cross-Coupling Reactions of Organoboron Compounds.", Chem. Rev., 1995, pp. 2457-2583, vol. 95(7).
Mongin, F., et al., "Deprotonation of furans using lithium magnesates.", *Tetrahedron Lett.*, 2005, pp. 7989-7992, vol. 46.
Nishimura et al, "Tissue-specific mRNA Expression Profiles of Human ATP-binding Cassette and Solute Carrier Transporter Superfamilies.", *Drug Metab. Pharmacokinet.*, 2005, pp. 452-477, vol. 20(6).
Nomura, S., "Renal Sodium-Dependent Glucose Cotransporter 2 (SGLT2) Inhibitors for New Anti-Diabetic Agent.", *Current Topics in Medicinal Chemistry*, 2010, pp. 411-418, vol.
Ohsumi et al. "Pyrazole-O-Glucosides as Novel Na+-Glucose Cotransporter (SGLT) Inhibitors.", Bioorganic & Medicinal Chemistry Letters, 2003, pp. 2269-2272, vol. 13.
Oku et al., "T-1095, an Inhibitor of Renal Na+-Glucose Cotransporters, May Provide a Novel Approach to Treating Diabetes.", Diabetes, Sep. 1999, pp. 1794-1800, vol. 48.
Orjales et al. "New 2-Piperazinylbenzimidazole Derivatives as 5-HT-3 Antagonists. Synthesis and Pharmacological Evaluation.", J. Med. Chem., 1997, pp. 586-593, vol. 40.
Parker et al., "Reductive Aromatization of Quinols: Synthesis of the C-Arylglycoside Nucleus of the Paulacandins and Chaetiacandin.", *Organic Letters*, 2000, pp. 497-499, vol. 2(4).
Parrott, E.L., "Milling of pharmaceutical solids.", Journal of Pharmaceutical Sciences, Jun. 1974, pp. 813-829, vol. 63(6).
Patani et al., "Bioisosterism: A Rational Approach in Drug Design.", Chem. Rev., American Chemical Society, 1996, pp. 3147-3176, vol. 96.
Peng et al., "Post-transcriptional Regulaton of Na+/Glucose Cotransporter (SGTL1) Gene Expression in LLC-PK1 Cells.", Journal of Biological Chemistry, 1995, pp. 20536-20542, vol. 270(35).
*Perry's Chemical Engineers Handbook*, Sixth Edition, 1984, pp. 21-13 to 21-19.
*Pharmaceutical Sciences*, Remington, 17th Ed., pp. 1585-1594 (1985).
Polshettiwar et al., "Pd-N-heterocycle carbene (NHR) organic silica: synthesis and application in carbon-carbon coupling reactions.", Tetrahedron, May 12, 2008, pp. 4637-4643, vol. 64(20), Elsevier Science Publishers, Amsterdam, NL, XP022607642.
Raynaud et al., "Revised Concept for the Estimation of Insulin Sensitivity From a Single Sample.", Diabetes Care, Jun. 1999, pp. 1003-1004, vol. 22(6).
Rosenstock et al., "Canagliflozin, an Inhibitor of Sodium Glucose Co-Transporter 2 (SGLT2), Improves Glycemic Control and Lowers Body Weight in Subjects with Type 2 Diabetes (T2D) on Metformin.", Diabetes, Jun. 1, 2010, pp. A21, vol. 59(supp. 1), American Diabetes Association, US, XP009139979.
Rosetti et al., "Correction of Hyperglycemia with Phlorizin Normalizes Tissue Sensitivity to Insulin in diabetic rats.", *Journal of Clinical Investigation*, 1987, pp. 1510-1515, vol. 79.
Rosetti et al., "Effect of Chronic Hyperglycemia on In Vivo Insulin Secretion in Partially Pancreatectomized Rats.", *Journal of Clinical Investigation*, 1987, pp. 1037-1044, vol. 80.
Rosetti et al., "Glucose Toxicity."; *Diabetes Care* 1990, pp. 610-630, vol. 13.
Schmidt et al., "Synthese von Pyrazol-, Pyrazolo[3,4-d]pyrimidin- und 1H-1,2,4-Triazolgluconucleosiden aus Glucosehydrazonen.", Liebigs Ann. Chem., 1981, pp. 2309-2317.
Silverman, R. B., *"The Organic Chemistry of Drug Design and Drug Action"*, Academic Press, 1992, pp. 19-23.
Somei et al., "The First and Simple Total Synthesis of Cappariloside Al.", *Heterocycles*, 2000, pp. 1573-1578, vol. 53(7).
Srogl et al., "Sulfonium salts. Participants par excellence in metal-catalyzed carbon-carbon bond-forming reactions.", *Journal of the American Chemical Society*, Jan. 1, 1997, pp. 12376-12377, vol. 119, American Chemical Society, US, XP002955770.
Stoner et al., "Benzylation via Tandem Grignard Reaction—Lodotrimethylsilane (TMSI) Mediated.Reduction.", *Tetrahedron*, 1995, pp. 11043-11062, vol. 51(41).
Stumvoll et al., "Use of the Oral Glucose Tolerance Test to Assess Insulin Release and Insulin Sensitivity.", *Diabetes Care*, Mar. 2000, pp. 295-301, vol. 23(3).
Tanaka et al. "Solid-Phase Synthesis of --Mono-Substituted Ketones and an Application to the Synthesis of a Library of Phlorizin Derivatives.", *Synlett*, 2002, pp. 1427-1430, No. 9.
Thornber, C.T., "Isosterism and Molecular Modification in Drug Design.", *Chem. Society Review*, 1979, pp. 563-580, vol. 8.
Tilak et al, "Carcinogenesis by Thiophene Isosters of Polycyclic Hydrocarbons.", Tetrahedron, 1960, pp. 76-95, vol. 9.
Tsujihara et al., "Na+ Glucose Cotransporter (SGLT) Inhibitors as Antidiabetic Agents. 4. Synthesis and Pharmacological Properties of 4'-Dehydroxyphlorizin Derivatives Substituted on the B Ring.", *Journal of Medicinal Chemistry*, 1999, pp. 5311-5324, vol. 42.
Tsujihara et al., *Bio Clinica*, 1998, pp. 324-328, vol. 13(4), English language Abstract.
Turk et al., "Glucose/galactose malabsorption caused by a defect in the Na+/glucose cotransporter.", *Nature*, Mar. 1991, pp. 354-356, vol. 350.
Ueta et al., "Long-term treatment with the Na+-glucose contransporter inhibitor T1095 causes sustained improvement in hyperglycemia and prevents diabetic neuropathy in Goto-Kakizaki Rats.", *Life Sci.*, 2005, pp. 2655-2668, vol. 76(23).
Unger et al., "Hyperglycemia as an inducer as well as a consequence of impaired islet cell function and insulin resistance: implications for the management of diabetes.", *Diabetologia*, 1985, pp. 119-121, vol. 28.
Vippagunta et al., "Crystalline Solids." *Advanced Drug Delivery Reviews*, 2001, pp. 3-26, vol. 48.
Wallace et al., "Use and Abuse of Homa Modeling.", *Diabetes Care*, Jun. 2004, pp. 1487-1495, vol. 27(6).
Wang et al, "Selective monolithiation of 2,5-dibromopyridine with butyllithium" *Tetrahedron Letters*, 2000, pp. 4335-4338, vol. 41.
Wareham et al., "Is There Really an epidemic of diabetes?", *Diabetologia* 2005, pp. 1454-1455, vol. 48.
Washburn, W. N., "Evolution of sodium glucose co-transporter 2 inhibitors as anti-diabetic agents.", *Expert Opin. Ther. Patents*, 2009, pp. 1485-1499, vol. 19(11).

(56) References Cited

OTHER PUBLICATIONS

Watanabe et al., "Cyclopentyl Methyl Ether as a New and Alternative Process Solvent.", *Organic Process Research and Development*, 2007, pp. 251-258, vol. 11.

Wild et al., "Global Prevalence of Diabetes: Estimates for the year 2000 and projections for 2030.", *Diabetes Care*, May 2004, pp. 1047-1053, vol. 27(5).

Wolff, M. E., vol. 1: *Principles and Practice*, Burger's Medicinal Chemistry and Drug Discovery, 5th Edition, 1995, pp. 975-977.

Wright, E.M., "Renal Na+-glucose cotransporters.", *Am J Physiol Renal Physiol*, 2001, pp. F10-F18, vol. 280.

Wurster D.E., "Air-suspension Technique of Coating Drug Particles* A Preliminary Report.", *Journal of the American Pharmaceutical Association*, Aug. 1959, pp. 451-454, vol. 48(8).

Wurster, D.E., "Preparation of compressed tablet granulations by the air-suspension technique II.", *Journal of the American Pharmaceutical Association*, 1960, pp. 82-84, vol. 49(2).

Yang et al., "Convergent C-Glycolipid Synthesis via the Ramberg-Backlund Reaction: Active Antiproliferative Glycolipids.", *Org. Lett.* 1999, pp. 2149-2151, vol. 1913).

Yoshimura et al., "Discovery of Novel and PotenCRetinoic Acid Receptor alpha—Agonists: Synthesis and Evaluation of Benzofuranyl-pyrrole and Benzothiophenyl-pyrrole Derivatives.", *J. Med. Chem.*, 2000, pp. 2929-2937, vol. 43.

Zamani et al., "Synthesis and Structure Determination of Some New N-Glycosides of 4,5-Disubstituted-1,2,4-triazole-3-thiones.", *Journal of the Chinese Chemical Society*, 2002, pp. 1041-1044, vol. 49.

Zhdanov, Y. et al., "Application of organozinc compounds in the synthesis of carbon-carbon derivatives of sugars.", Database CA (online), Chemical Abstracts Service, Columbus, Ohio, USA, XP002612365, 1958.

Translation—Zhdanov, Y. et al., "Application of organozinc compounds in the synthesis of carbon-carbon derivatives of sugars.", Database CA (online), Chemical Abstracts Service, Columbus, Ohio, USA, XP002612365, 1958.

Zhou, F. Y., "The Synthesis and Characterization of 1-Benzyl-3-N-(Beta-D-glucosie-1-yl)-4-fluorouracil.", *Hecheng Huaxue*, 2001, pp. 272-274, vol. 9(3).

International Search Report relating to International Patent Application No. PCT/US2012/037062. Date of Mailing of International Search Report: Aug. 8, 2012.

Bavin, M., "Process Development: Polymorphism in Process Development.", Chemistry & Industry, 1989, pp. 527-529, vol. 16.

Jianqun, et al., "Recent advances in palladium catalysts for aryl chlorides coupling reaction", *Industrial Catalysis* Jul. 31, 2005, pp. 29-44, vol. 13(7).

Asahara et al., *Handbook of Solvents*, K.K. Kodansha., Sep. 1, 1985, Sixth Printing, pp. 47-51, Tokyo, JP.

Kozikowski et al., "Organometallics in Organic Synthesis. Applications of a New Diorganozinc Reaction to the Synthesis of C-Glycosyl Compounds With Evidence for an Oxonium-Ion Mechanism.", Carbohydrate Research, 1987, pp. 109-124, vol. 171.

Zhiyin, et al., "Cross-coupling reaction of Grignard reagent with thiophenyl halides by using nickel phosphine as catalyst and the synthesis of a-terthienyl", *Huaxue Shiji*, Dec. 31, 1995, pp. 289-290, vol. 17(5).

\* cited by examiner

Peak-picked pXRD spectrum for the crystalline
L-proline co-crystal of the compound of formula (I-X)

Peak-picked pXRD spectrum for the crystalline citric acid co-crystal of the compound of formula (I-X)

DSC scan for crystalline L-proline co-crystal of the compound of formula (I-X)

DSC scan for crystalline citric acid co-crystal of the compound of formula (I-X)

L-PROLINE AND CITRIC ACID CO-CRYSTALS OF (2S, 3R, 4R, 5S,6R)-2-(3-((5-(4-FLUOROPHENYL)THIOPEN-2-YL) METHYL)4-METHYLPHENYL)-6-(HYDROXYMETHYL)TETRAHYDRO-2H-PYRAN-3,4,5-TRIOL

CROSS REFERENCE TO RELATED APPLICATIONS

This application claims the benefit of U.S. Provisional Application 61/483,887 filed on May 9, 2011, which is incorporated by reference herein in its entirety.

FIELD OF THE INVENTION

The present invention is directed to L-proline and citric acid co-crystals of (2S,3R,4R,5S,6R)-2-(3-((5-(4-fluorophenyl)thiophen-2-yl)methyl)-4-methylphenyl)-6-(hydroxymethyl)tetrahydro-2H-pyran-3,4,5-triol, pharmaceutical compositions containing said co-crystals and their use in the treatment of glucose-related disorders such as Type 2 diabetes mellitus and Syndrome X.

BACKGROUND OF THE INVENTION

Diabetes mellitus is a medical term for the presence of elevated blood glucose. People with diabetes either don't produce insulin, produce too little insulin or do not respond to insulin, resulting in the buildup of glucose in the blood. The most common form of diabetes is Type 2 diabetes, once referred to as adult onset diabetes or non-insulin dependent diabetes (NIDDM), which may account for >90% of diabetes in adults. However, as the younger population becomes increasingly overweight or obese, Type 2 diabetes is becoming more prevalent in teens and children. Diabetes may also refer to gestational diabetes, Type 1 diabetes or autoimmune diabetes, once referred to as juvenile onset diabetes and type 1½ diabetes, also referred to as latent-autoimmune diabetes in adults or LADA. Diabetes may occur because of poor dietary habits or lack of physical activity (e.g., sedentary lifestyle), genetic mutations, injury to the pancreas, drug (e.g., AIDS therapies) or chemical (e.g., steroid) exposure or disease (e.g., cystic fibrosis, Down syndrome, Cushing's syndrome). Two rare types of genetic defects leading to diabetes are termed maturity-onset diabetes of the young (MODY) and atypical diabetes mellitus (ADM).

Type 2 diabetes mellitus (non-insulin-dependent diabetes mellitus or NIDDM) is a metabolic disorder involving dis-regulation of glucose metabolism and insulin resistance, and long-term complications involving the eyes, kidneys, nerves, and blood vessels. Type 2 diabetes mellitus usually develops in adulthood (middle life or later) and is described as the body's inability to make either sufficient insulin (abnormal insulin secretion) or its inability to effectively use insulin (resistance to insulin action in target organs and tissues). More particularly, patients suffering from Type 2 diabetes mellitus have a relative insulin deficiency. That is, in these patients, plasma insulin levels are normal to high in absolute terms, although they are lower than predicted for the level of plasma glucose that is present.

Type 2 diabetes mellitus is characterized by the following clinical signs or symptoms: persistently elevated plasma glucose concentration or hyperglycemia; polyuria; polydipsia and/or polyphagia; chronic microvascular complications such as retinopathy, nephropathy and neuropathy; and macrovascular complications such as hyperlipidemia and hypertension which can lead to blindness, end-stage renal disease, limb amputation and myocardial infarction.

Syndrome X, also termed Insulin Resistance Syndrome (IRS), Metabolic Syndrome, or Metabolic Syndrome X, is a disorder that presents risk factors for the development of Type 2 diabetes mellitus and cardiovascular disease including glucose intolerance, hyperinsulinemia and insulin resistance, hypertriglyceridemia, hypertension and obesity.

The diagnosis of Type 2 diabetes mellitus includes assessment of symptoms and measurement of glucose in the urine and blood. Blood glucose level determination is necessary for an accurate diagnosis. More specifically, fasting blood glucose level determination is a standard approach used. However, the oral glucose tolerance test (OGTT) is considered to be more sensitive than fasted blood glucose level. Type 2 diabetes mellitus is associated with impaired oral glucose tolerance (OGT). The OGTT thus can aid in the diagnosis of Type 2 diabetes mellitus, although generally not necessary for the diagnosis of diabetes (EMANCIPATOR K, *Am J Clin Pathol* 1999 November; pp 665-674, Vol. 112(5):665-74; Type 2 Diabetes Mellitus, Decision Resources Inc., March 2000). The OGTT allows for an estimation of pancreatic beta-cell secretory function and insulin sensitivity, which helps in the diagnosis of Type 2 diabetes mellitus and evaluation of the severity or progression of the disease (e.g., CAUMO, A., et al., *J Clin Endocrinol Metab,* 2000, pp 4396-4402, Vol. 85(11)). More particularly, the OGTT is extremely helpful in establishing the degree of hyperglycemia in patients with multiple borderline fasting blood glucose levels that have not been diagnosed as diabetics. In addition, the OGTT is useful in testing patients with symptoms of Type 2 diabetes mellitus where the possible diagnosis of abnormal carbohydrate metabolism has to be clearly established or refuted.

Thus, impaired glucose tolerance is diagnosed in individuals that have fasting blood glucose levels less than those required for a diagnosis of Type 2 diabetes mellitus, but have a plasma glucose response during the OGTT between normal and diabetics. Impaired glucose tolerance is considered a pre-diabetic condition, and impaired glucose tolerance (as defined by the OGTT) is a strong predictor for the development of Type 2 diabetes mellitus (HAFFNER, S. M., *Diabet Med,* 1997 August; 14 Suppl 3:S12-8).

Type 2 diabetes mellitus is a progressive disease associated with the reduction of pancreatic function and/or other insulin-related processes, aggravated by increased plasma glucose levels. Thus, Type 2 diabetes mellitus usually has a prolonged pre-diabetic phase and various pathophysiological mechanisms can lead to pathological hyperglycemia and impaired glucose tolerance, for instance, abnormalities in glucose utilization and effectiveness, insulin action and/or insulin production in the prediabetic state (GOLDBERG, R. B., *Med Clin North Am,* 1998 July; pp 805-821, Vol. 82(4)).

The pre-diabetic state associated with glucose intolerance can also be associated with a predisposition to abdominal obesity, insulin resistance, hyperlipidemia, and high blood pressure, that is, Syndrome X (GROOP L, et al., *Am J Hypertens,* 1997 September; 10(9 Pt 2):172S-180S; HAFFNER, S. M., *J Diabetes Complications,* 1997 March-April; pp 69-76, Vol. 11(2); BECK-NIELSEN, H., et al., *Diabet Med,* 1996 September; 13(9 Suppl 6):S78-84).

Thus, defective carbohydrate metabolism is pivotal to the pathogenesis of Type 2 diabetes mellitus and impaired glucose tolerance (DIUNNEEN, S. F., *Diabet Med,* 1997 August; 14 Suppl 3:S19-24). In fact, a continuum from impaired glucose tolerance and impaired fasting glucose to definitive Type 2 diabetes mellitus exists (RAMLO-HAL-STED, B. A., et al., *Prim Care,* 1999 December; pp 771-789, Vol. 26(4)).

Early intervention in individuals at risk to develop Type 2 diabetes mellitus, focusing on reducing the pathological hyperglycemia or impaired glucose tolerance may prevent or delay the progression towards Type 2 diabetes mellitus and associated complications and/or Syndrome X. Therefore, by effectively treating impaired oral glucose tolerance and/or elevated blood glucose levels, one can prevent or inhibit the progression of the disorder to Type 2 diabetes mellitus or Syndrome X.

Typical treatment of glucose disorders including Type 2 diabetes mellitus and Syndrome X focuses on maintaining the blood glucose level as near to normal as possible and includes diet and exercise, and when necessary, treatment with anti-diabetic agents, insulin or a combination thereof. Type 2 diabetes mellitus that cannot be controlled by dietary management is treated with oral antidiabetic agents including, but not limited to, sulfonylureas (e.g., not limited to first generation: chlorpropamide, tolazamide, tolbutamide; second generation: glyburide, glipizide; and third generation: glimepiride), biguanides (e.g., metformin), thiazolidinediones (e.g., rosiglitazone, pioglitazone, troglitazone), alpha-glucosidase inhibitors (e.g., acarbose, miglitol), meglitinides (e.g., repaglinide), other insulin-sensitizing compounds, and/or other anti-obesity agents (e.g., orlistat or sibutramine). For Syndrome X, the anti-diabetic agents are additionally combined with pharmacological agents for the treatment of the concomitant co-morbidities (e.g., antihypertensives for hypertension, hypolipidemic agents for hyperlipidemia).

First-line therapies typically include metformin and sulfonylureas as well as thiazolidinediones. Metformin monotherapy is a first line choice, particularly for treating Type 2 diabetic patients who are also obese and/or dyslipidemic. Lack of an appropriate response to metformin is often followed by treatment with metformin in combination with sulfonylureas, thiazolidinediones, or insulin. Sulfonylurea monotherapy (including all generations of drugs) is also a common first line option. Another first line therapy choice may be thiazolidinediones. Patients who do not respond appropriately to oral anti-diabetic monotherapy, are given combinations of these agents. When glycemic control cannot be maintained with oral antidiabetics alone, insulin therapy is used either as a monotherapy, or in combination with oral antidiabetic agents. These same strategies, optionally in combination with additional strategies (e.g., anti-hypertensive) can be used for the treatment of Syndrome X.

In addition to antidiabetic agents, therapies may include add-on treatment with anti-obesity agents such as orlistat, a pancreatic lipase inhibitor, which prevents the breakdown and absorption of fat; or sibutramine, an appetite suppressant and inhibitor of the reuptake of serotonin, norepinephrine and dopamine in the brain. Other potential add-on anti-obesity agents include, but are not limited to, appetite-suppressants acting through adrenergic mechanisms such as benzphetamine, phenmetrazine, phentermine, diethylpropion, mazindol, sibutramine, phenylpropanolamine or, ephedrine; appetite-suppressant agents acting through serotonergic mechanisms such as quipazine, fluoxetine, sertraline, fenfluramine, or dexfenfluramine; appetite-suppressant agents acting through dopamine mechanisms, eg, apomorphine; appetite-suppressant agents acting through histaminergic mechanisms (eg, histamine mimetics, H3 receptor modulators); enhancers of energy expenditure such as beta-3 adrenergic agonists and stimulators of uncoupling protein function; leptin and leptin mimetics; neuropeptide Y antagonists; melanocortin-1, 3 and 4 receptor modulators; cholecystokinin agonists; glucagon-like peptide-1 (GLP-1) mimetics and analogues (eg, Exendin); androgens (eg, dehydroepiandrosterone and derivatives such as etiocholandione), testosterone, anabolic steroids (eg, oxandrolone), and steroidal hormones; galanin receptor antagonists; cytokine agents such as ciliary neurotrophic factor; amylase inhibitors; enterostatin agonists/mimetics; orexin/hypocretin antagonists; urocortin antagonists; bombesin agonists; modulators of protein kinase A; corticotropin-releasing factor mimetics; cocaine- and amphetamine-regulated transcript mimetics; calcitonin-gene related peptide mimetics; and fatty acid synthase inhibitors.

There remains a need to provide an effective treatment for glucose-related disorders such as elevated glucose levels, Type 2 diabetes mellitus, Syndrome X, and the like. There also remains a need to provide an effective treatment for glucose related disorders which also slows or prevents the progression and/or development of Type 2 diabetes mellitus.

SUMMARY OF THE INVENTION

The present invention is directed to an L-proline co-crystal of a compound of formula (I-X)

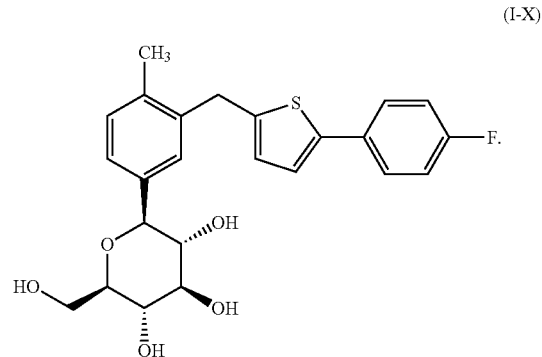 [SMILES: Cc1ccc([C@@H]2O[C@H](CO)[C@@H](O)[C@H](O)[C@H]2O)cc1Cc1ccc(-c2ccc(F)cc2)s1]

(I-X)

The present invention is further directed to a citric acid co-crystal of the compound of formula (I-X)

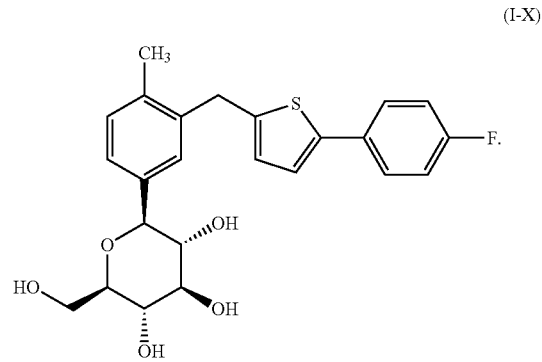 [SMILES: Cc1ccc([C@@H]2O[C@H](CO)[C@@H](O)[C@H](O)[C@H]2O)cc1Cc1ccc(-c2ccc(F)cc2)s1]

(I-X)

Preferably, the L-proline and citric acid co-crystals of the compound of formula (I-X) of the present invention are crystalline. The present invention is further directed to processes for the preparation of the co-crystals of a compound of formula (I-X), as herein described in more detail.

Illustrative of the invention is a pharmaceutical composition comprising a pharmaceutically acceptable carrier and a co-crystal former of the compound of formula (I-X), as described herein. An illustration of the invention is a pharmaceutical composition made by mixing a co-crystal former of the compound of formula (I-X), as described herein and a pharmaceutically acceptable carrier. Illustrating the invention is a process for making a pharmaceutical composition comprising mixing a co-crystal former of the compound of formula (I-X), as described herein and a pharmaceutically acceptable carrier.

The present invention is further directed to methods for the treatment and/or prevention of glucose-related disorders, said methods comprising administering to a subject in need thereof a crystalline co-crystal of the compound of formula (I-X) as described herein.

DETAILED DESCRIPTION OF THE INVENTION

Figure 1:
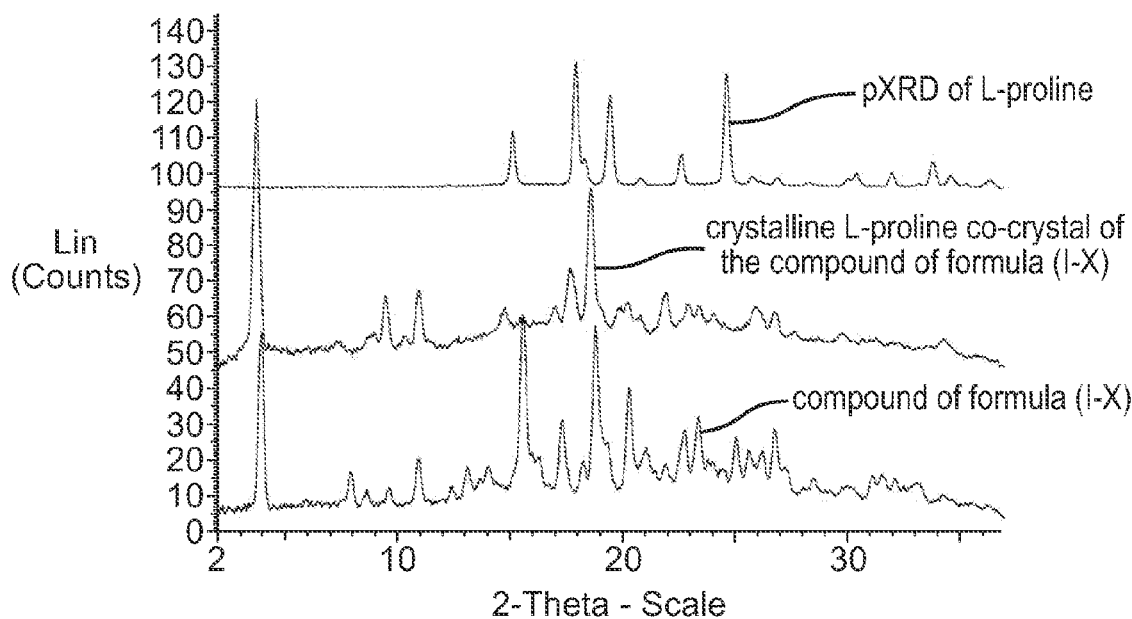
FIG. 1 illustrates a representative pXRD spectrum of L-proline (top), the compound of formula (I-X) (bottom) and the crystalline L-proline co-crystal of the compound of formula (I-X) (middle).

The present invention is directed to co-crystals of a compound of formula (I-X)

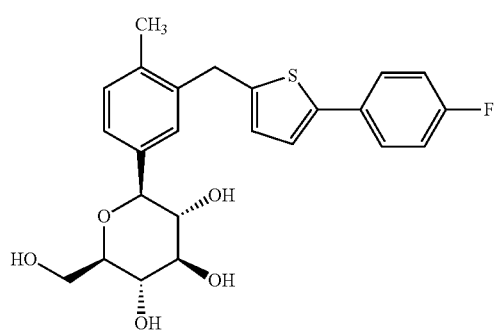

(I-X)

(also known as (2S,3R,4R,5S,6R)-2-(3-((5-(4-fluorophenyl)thiophen-2-yl)methyl)-4-methylphenyl)-6-(hydroxymethyl)tetrahydro-2H-pyran-3,4,5-triol). More particularly, the present invention is directed to an L-proline co-crystal of the compound of formula (I-X); and a citric acid co-crystal of the compound of formula (I-X). In an embodiment of the present invention, the L-proline co-crystal of the compound of formula (I-X) is crystalline. In another embodiment of the present invention, the citric acid co-crystal of the compound of formula (I-X) is crystalline.

The compound of the formula (I-X) exhibits an inhibitory activity against sodium-dependent glucose transporter, such as for example SGLT2. The compound of formula (I-X) may be prepared according to the process as disclosed in Nomura, S. et al., US Patent Publication, US 2005/0233988 A1, published Oct. 20, 2005, which is incorporated by reference herein.

The present invention is further directed to methods for the treatment and/or prevention of glucose-related disorders (preferably Type 2 diabetes mellitus), said methods comprising administering to a subject in need thereof a co-crystal of the compound of formula (I-X), as described herein.

As used herein, the notation "*" shall denote the presence of a stereogenic center.

Where the compounds according to this invention have at least one chiral center, they may accordingly exist as enantiomers. Where the compounds possess two or more chiral centers, they may additionally exist as diastereomers. It is to be understood that all such isomers and mixtures thereof are encompassed within the scope of the present invention. Preferably, wherein the compound is present as an enantiomer, the enantiomer is present at an enantiomeric excess of greater than or equal to about 80%, more preferably, at an enantiomeric excess of greater than or equal to about 90%, more preferably still, at an enantiomeric excess of greater than or equal to about 95%, more preferably still, at an enantiomeric excess of greater than or equal to about 98%, most preferably, at an enantiomeric excess of greater than or equal to about 99%. Similarly, wherein the compound is present as a diastereomer, the diastereomer is present at an diastereomeric excess of greater than or equal to about 80%, more preferably, at an diastereomeric excess of greater than or equal to about 90%, more preferably still, at an diastereomeric excess of greater than or equal to about 95%, more preferably still, at an diastereomeric excess of greater than or equal to about 98%, most preferably, at an diastereomeric excess of greater than or equal to about 99%.

Furthermore, some of the crystalline forms for the compounds of the present invention may exist as polymorphs and as such are intended to be included in the present invention. In addition, some of the compounds of the present invention may form solvates with water (i.e., hydrates) or common organic solvents, and such solvates are also intended to be encompassed within the scope of this invention.

As used herein, unless otherwise noted, the term "isolated form" shall mean that the compound is present in a form which is separate from any solid mixture with another compound(s), solvent system or biological environment.

In an embodiment of the present invention, the L-proline co-crystal of the compound of formula (I-X) is present in an isolated form. In another embodiment of the present invention, the citric acid co-crystal of the compound of formula (I-X) is present in an isolated form.

As used herein, unless otherwise noted, the term "substantially pure form" shall mean that the mole percent of impurities in the isolated crystalline form is less than about 5 mole percent, preferably less than about 2 mole percent, more preferably, less than about 0.5 mole percent, most preferably, less than about 0.1 mole percent. In an embodiment of the present invention, the L-proline co-crystal of the compound of formula (I-X) is present as a substantially pure form. In another embodiment of the present invention, the citric acid co-crystal of the compound of formula (I-X) is present as a substantially pure form.

The present invention is further directed to methods for the treatment and prevention of (preferably, the prevention of the development of) glucose related disorders comprising administering to a subject in need thereof a therapeutically effective amount of any of the co-crystals of the compound of formula (I-X) as herein described.

The methods of the present inventions are directed to the treatment and or prevention (including delay in the progression or onset of) of "glucose-related disorders". As used herein, the term "glucose related disorder" shall be defined as any disorder which is characterized by or is developed as a consequence of elevated glucose levels. Glucose-related disorders shall include diabetes mellitus, diabetic retinopathy, diabetic neuropathy, diabetic nephropathy, delayed wound healing, insulin resistance, hyperglycemia, hyperinsulinemia, elevated blood levels of fatty acids, elevated blood levels of glucose, hyperlipidemia, obesity, hypertriglyceridemia, Syndrome X, diabetic complications, atherosclerosis, or hypertension. In particular, the "glucose related-disorder" is diabetes mellitus (type 1 and type 2 diabetes mellitus, etc.), diabetic complications (such as diabetic retinopathy, diabetic neuropathy, diabetic nephropathy), obesity, or postprandial hyperglycemia.

In an embodiment of the present invention, the glucose related disorder is selected from the group consisting of diabetes mellitus, diabetic retinopathy, diabetic neuropathy, diabetic nephropathy, delayed wound healing, insulin resistance, hyperglycemia, hyperinsulinemia, elevated blood levels of fatty acids, hyperlipidemia, obesity, hypertriglyceridemia, Syndrome X, diabetic complications, atherosclerosis and hypertension.

In another embodiment of the present invention, glucose related disorder is selected from the group consisting of type 1 diabetes mellitus, type 2 diabetes mellitus, diabetic retinopathy, diabetic neuropathy, diabetic nephropathy, obesity and postprandial hyperglycemia. In another embodiment of the present invention, the glucose related disorder is selected from the group consisting of type 1 diabetes mellitus, type 2 diabetes mellitus, diabetic retinopathy, diabetic neuropathy, diabetic nephropathy, obesity, and delayed wound healing. In another embodiment of the present invention, the glucose related disorders is selected from the group consisting of poor glycemic control, Type 2 Diabetes Mellitus, Syndrome X, gestational diabetes, insulin resistance, hyperglycemia. In another embodiment of the present invention, the glucose related disorder is Type 2 diabetes mellitus.

In another embodiment, the glucose related disorder is selected from the group consisting of elevated glucose level, pre-diabetes, impaired oral glucose tolerance, poor glycemic control, Type 2 Diabetes Mellitus, Syndrome X (also known as metabolic syndrome), gestational diabetes, insulin resistance, and hyperglycemia.

Treatment of glucose related disorders may comprise lowering glucose levels, improving glycemic control, decreasing insulin resistance and/or preventing the development of a glucose related disorder (for example preventing a patient suffering from impaired oral glucose tolerance or elevated glucose levels from developing Type 2 diabetes mellitus).

As used herein, the terms "Syndrome X", "Metabolic Syndrome" and "Metabolic Syndrome X" shall mean a disorder that presents risk factors for the development of Type 2 diabetes mellitus and cardiovascular disease and is characterized by insulin resistance and hyperinsulinemia and may be accompanied by one or more of the following: (a) glucose intolerance, (b) Type 2 diabetes mellitus, (c) dyslipidemia, (d) hypertension and (e) obesity.

As used herein, unless otherwise noted, the terms "treating", "treatment" and the like, shall include the management and care of a subject or patient (preferably mammal, more preferably human) for the purpose of combating a disease, condition, or disorder and includes the administration of a compound of the present invention to prevent the onset of the symptoms or complications, alleviate the symptoms or complications, or eliminate the disease, condition, or disorder.

As used herein, unless otherwise noted, the term "prevention" shall include (a) reduction in the frequency of one or more symptoms; (b) reduction in the severity of one or more symptoms; (c) the delay or avoidance of the development of additional symptoms; and/or (d) delay or avoidance of the development of the disorder or condition.

One skilled in the art will recognize that wherein the present invention is directed to methods of prevention, a subject in need of thereof (i.e. a subject in need of prevention) shall include any subject or patient (preferably a mammal, more preferably a human) who has experienced or exhibited at least one symptom of the disorder, disease or condition to be prevented. Further, a subject in need thereof may additionally be a subject (preferably a mammal, more preferably a human) who has not exhibited any symptoms of the disorder, disease or condition to be prevented, but who has been deemed by a physician, clinician or other medical profession to be at risk of developing said disorder, disease or condition. For example, the subject may be deemed at risk of developing a disorder, disease or condition (and therefore in need of prevention or preventive treatment) as a consequence of the subject's medical history, including, but not limited to, family history, pre-disposition, co-existing (comorbid) disorders or conditions, genetic testing, and the like.

The term "subject" as used herein, refers to an animal, preferably a mammal, most preferably a human, who has been the object of treatment, observation or experiment. Preferably, the subject has experienced and/or exhibited at least one symptom of the disease or disorder to be treated and/or prevented.

The term "therapeutically effective amount" as used herein, means that amount of active compound or pharmaceutical agent that elicits the biological or medicinal response in a tissue system, animal or human that is being sought by a researcher, veterinarian, medical doctor or other clinician, which includes alleviation of the symptoms of the disease or disorder being treated.

Optimal dosages to be administered may be readily determined by those skilled in the art, and will vary with for example, the mode of administration, the strength of the preparation, the mode of administration, and the advancement of the disease condition. In addition, factors associated with the particular patient being treated, including patient age, weight, diet and time of administration, will result in the need to adjust dosages.

One skilled in the art will recognize that, both in vivo and in vitro trials using suitable, known and generally accepted cell and/or animal models are predictive of the ability of a test compound or co-therapy to treat or prevent a given disorder. One skilled in the art will further recognize that human clinical trials including first-in-human, dose ranging and efficacy trials, in healthy patients and/or those suffering from a given disorder, may be completed according to methods well known in the clinical and medical arts.

As used herein, the term "composition" is intended to encompass a product comprising the specified ingredients in the specified amounts, as well as any product which results, directly or indirectly, from combinations of the specified ingredients in the specified amounts.

To provide a more concise description, some of the quantitative expressions herein are recited as a range from about amount X to about amount Y. It is understood that wherein a range is recited, the range is not limited to the recited upper and lower bounds, but rather includes the full range from about amount X through about amount Y, or any amount or range therein.

To provide a more concise description, some of the quantitative expressions given herein are not qualified with the term "about". It is understood that whether the term "about" is used explicitly or not, every quantity given herein is meant to refer to the actual given value, and it is also meant to refer to the approximation to such given value that would reasonably be inferred based on the ordinary skill in the art, including approximations due to the experimental and/or measurement conditions for such given value.

Examples of suitable solvents, bases, reaction temperatures, and other reaction parameters and components are provided in the detailed descriptions which follows herein. One skilled in the art will recognize that the listing of said examples is not intended, and should not be construed, as limiting in any way the invention set forth in the claims which follow thereafter.

One skilled in the art will recognize that wherein a reaction step of the present invention may be carried out in a variety of solvents or solvent systems, said reaction step may also be carried out in a mixture of the suitable solvents or solvent systems.

Where the processes for the preparation of the compounds according to the invention give rise to mixture of stereoisomers, these isomers may be separated by conventional techniques such as preparative chromatography.

The compounds may be prepared in racemic form, or individual enantiomers may be prepared either by enantiospecific synthesis or by resolution. The compounds may, for example, be resolved into their component enantiomers by standard techniques, such as the formation of diastereomeric pairs by salt formation with an optically active acid, such as (−)-di-p-toluoyl-D-tartaric acid and/or (+)-di-p-toluoyl-L-tartaric acid followed by fractional crystallization and regeneration of the free base. The compounds may also be resolved by formation of diastereomeric esters or amides, followed by chromatographic separation and removal of the chiral auxiliary. Alternatively, the compounds may be resolved using a chiral HPLC column.

Additionally, chiral HPLC against a standard may be used to determine percent enantiomeric excess (% ee). The enantiomeric excess may be calculated as follows $$[(Rmoles-Smoles)/(Rmoles+Smoles)] \times 100\%$$

where Rmoles and Smoles are the R and S mole fractions in the mixture such that Rmoles+Smoles=1. The enantiomeric excess may alternatively be calculated from the specific rotations of the desired enantiomer and the prepared mixture as follows:

$$ee=([\alpha-obs]/[\alpha-max]) \times 100.$$

The present invention is directed to an L-proline co-crystal of the compound of formula (I-X), preferably a crystalline L-proline co-crystal of the compound of formula (I-X). The present invention is further directed to a citric acid co-crystal of the compound of formula (I-X), preferably a crystalline citric acid co-crystal of the compound of formula (I-X).

Preparation of Crystalline L-Proline and Citric Acid Co-Crystals:

The L-proline and citric acid co-crystals of the compound of formula (I-X) were prepared as part of co-crystal screening. Briefly, approximately 15 mg of the compound of formula (I-X) was added to each well in a 48 well grinding block along with approximately 1 molar equivalent of co-crystal-former (L-proline or citric acid, respectively) and 10 μl of solvent (selected from acetone, ethanol, isopropyl acetate, toluene, water). Six (6) individual experiments were performed for each co-crystal former (5 solvents and 1 dry well). Wells were subjected to 10 minutes of ball-mill grinding and were followed up with immediate analysis by pXRD.

The crystalline L-proline co-crystal of the compound of formula (I-X) was additionally prepared by slurrying the compound of formula (I-X) (~1 g) and L-proline in acetone at a 1:1 stoichiometry.

The crystalline citric acid co-crystal of the compound of formula (I-X) was additionally prepared by thermal crystallization of the compound of formula (I-X) (~1 g) and citric acid in isopropyl acetate at a 1:1 stoichiometry.

Physical and Chemical Stability of L-Proline and Citric Acid Co-Crystals:

The crystalline L-proline co-crystal of the compound of formula (I-X) was tested for physical stability by storing about 10 mg of the co-crystal in 10 mL serum crimp vials, under following conditions: (a) 5° C., sealed; (b) 25° C./60% RH, open; (c) 40° C., sealed; (d) 40° C./75% RH, open; (e) 60° C., sealed; and (f) 80° C., sealed; with stability data collected at 1 day, 1 week, 2 weeks and 4 weeks. The crystalline L-proline co-crystal of the compound of formula (I-X) was found to be physically stable up to 4 weeks under all these conditions, with no visible color changes.

Samples of the crystalline L-proline co-crystal of the compound of formula (I-X) being tested for physical stability, sampled at 1 day, 1 week, 2 weeks and 4 weeks, were further tested for chemical stability/degradation. Crystalline L-proline co-crystal of the compound of formula (I-X) (~10 mg) was diluted with a 50:50 water:acetonitrile solution (10 mL), and then further diluted 10 fold for HPLC measurements. At 1 day, 1 week, 2 weeks and 4 weeks, all crystalline L-proline co-crystal samples appeared chemically stable. No degradation peaks were observed and the measured % areas remained consistent at each time point.

The crystalline citric acid co-crystal of the compound of formula (I-X) was similarly tested for physical stability by storing about 10 mg of the co-crystal in mL serum crimp vials, under following conditions: (a) 5° C., sealed; (b) 25° C./60% RH, open; (c) 40° C., sealed; (d) 40° C./75% RH, open; (e) 60° C., sealed; and (f) 80° C., sealed; with stability data collected at 1 day, 1 week, 2 weeks and 4 weeks. The crystalline citric acid co-crystal of the compound of formula (I-X) was found to be physically stable up to 4 weeks under these conditions, although a small amount of degradation (<0.3% on a peak basis) was observed when stored at 25° C./60% RH, when stored at 40° C./75% RH and when stored at either 60° C., or 80° C.

Samples of the crystalline citric acid co-crystal of the compound of formula (I-X) being tested for physical stability, sampled at 1 day, 1 week, 2 weeks and 4 weeks, were further tested for chemical stability/degradation. Crystalline citric acid co-crystal of the compound of formula (I-X) (~10 mg) was diluted with a 50:50 water:acetonitrile solution (10 mL), and then further diluted 10 fold for HPLC measurements. At 1 day, 1 week, 2 weeks and 4 weeks, all crystalline citric acid co-crystal samples appeared chemically stable when stored at 5° C., sealed and 40° C., sealed. A small degradation peak was observed in the 1 week, 2 week and 4 week, samples stored at 25° C./60% RH, open and samples stored at 60° C., sealed; although peak purity of these sample remained at >99%. A few small degradation peaks were also observed in the 1 week, 2 week and 4 week samples stored at 40° C./75% RH, open and 80° C., sealed; although peak purity for these samples also remained >99%.

pXRD, DSC, TGA and DVS Measurements:

The crystalline L-proline co-crystal of the compound of formula (I-X) and the crystalline citric acid co-crystal of the compound of formula (I-X) were further characterized via powder X-ray diffraction (pXRD), dynamic scanning calorimetry (DSC), thermogravimetric analysis (TGA and dynamic vapor sorption/desorption (DVS).

pXRD: Powder X-ray powder diffraction patterns were obtained using the Bruker AXS D8 Discover x-ray Diffractometer equipped with GADDS™ (General Area Diffraction Detection System), a Bruker AXS HI-STAR Area Detector at a distance of 15.05 cm as per system calibration, a copper source (Cu/K$_\alpha$ 1.54056 Å), automated x-y-z stage, and 0.5 mm collimator. The sample was compacted into pellet form and mounted on the x-y-z stage. A diffractogram was acquired under ambient conditions at a power setting of 40 kV and 40 mA in reflection mode while the sample remained stationary. The exposure time was approximately 1 minute for each sample. The diffractogram obtained underwent a spatial remapping procedure to account for the geometrical pincushion distortion of the area detector then integrated along chi from −118.8 to −61.8 degrees and 2-theta 2.1-37 degrees at a step size of 0.02 degrees with normalization set to bin normalize. In addition to using the Jade software, diffraction patterns obtained on the Bruker machine were viewed using EVA software.

DSC: An aliquot of the sample was weighed into an aluminum hermetic sample pan. The sample pan was loaded into the apparatus (Q1000 Differential Scanning Calorimeter, TA Instruments), which was equipped with an autosampler. A thermogram was obtained by individually heating the sample at a rate of 10° C./min from T$_{min}$ (typically room temperature) to T$_{max}$ (typically 300° C.) using an empty aluminum hermetic pan as a reference. Dry nitrogen was used as a sample purge gas and was set at a flow rate of 50 ml/min. Thermal transitions were viewed and analyzed using the analysis software provided with the instrument.

TGA: An aliquot of the sample was transferred into a platinum sample pan. The pan was placed on the loading platform and was then automatically loaded into the apparatus (Q500 Thermogravimetric Analyzer, TA Instruments) using the control software. Thermograms were obtained by individually heating the sample at 10° C./min from T$_{min}$ (typically room temperature) to T$_{max}$ (typically 300° C.) under flowing dry nitrogen, with a sample purge flow rate of 60 ml/min and a balance purge flow rate of 40 ml/min. Thermal transitions (e.g. weight changes) were viewed and analyzed using the analysis software provided with the instrument.

DVS: Moisture sorption was characterized on a DVS-1 Instrument (Surface Measurement Systems, Allentown, Pa.). In each case, the sample was subject to a drying curve from ambient to 0% relative humidity (RH), followed by two cycles of sorption (from 0% RH to 90% RH) and desorption (from 90% RH to 0% RH) in 10% RH steps at 25° C. At each step the sample was allowed to equilibrate at a specific % RH and thus, stabilize in terms of weight gained or lost prior to the instrument moving to the next step within the method.

Crystalline L-Proline Co-Crystal Properties:

The crystalline L-proline co-crystal of the compound of formula (I-X) was characterized by powder X-ray diffraction (pXRD) patterns; comparing the co-crystal patterns with the pXRD patterns of the co-crystal components, more particularly the pXRD of the compound of formula (I-X) and the pXRD of the L-proline.

FIG. 1 which follows herein, illustrates representative measured pXRD patterns for L-proline (top), the compound of formula (I-X) (bottom) and the crystalline L-proline co-crystal of the compound of formula (I-X) (middle).

In an embodiment, the crystalline L-proline co-crystal of the compound of formula (I-X) may be characterized by its powder X-ray diffraction pattern, comprising the peaks as listed in Table 1, below.

TABLE 1

Crystalline L-proline Co-Crystal of Compound of Formula (I-X)

| No. | Position [°2θ] | d-spacing [Å] | Relative Intensity [%] |
|---|---|---|---|
| 1 | 3.76 | 23.50 | 92 |
| 2 | 9.52 | 9.29 | 49 |
| 3 | 10.99 | 8.05 | 22 |
| 4 | 16.99 | 5.22 | 24 |
| 5 | 17.84 | 4.97 | 100 |
| 6 | 18.63 | 4.76 | 92 |
| 7 | 19.93 | 4.46 | 26 |
| 8 | 20.88 | 4.25 | 20 |
| 9 | 21.96 | 4.05 | 44 |
| 10 | 23.42 | 3.80 | 43 |
| 11 | 25.92 | 3.44 | 23 |
| 12 | 26.77 | 3.33 | 30 |

Preferably, the crystalline L-proline co-crystal of the compound of formula (I-X) is characterized by its pXRD pattern which comprises peaks having a relative intensity greater than or equal to about 25%, preferably having a relative intensity greater than or equal to about 40%.

Figure 2:
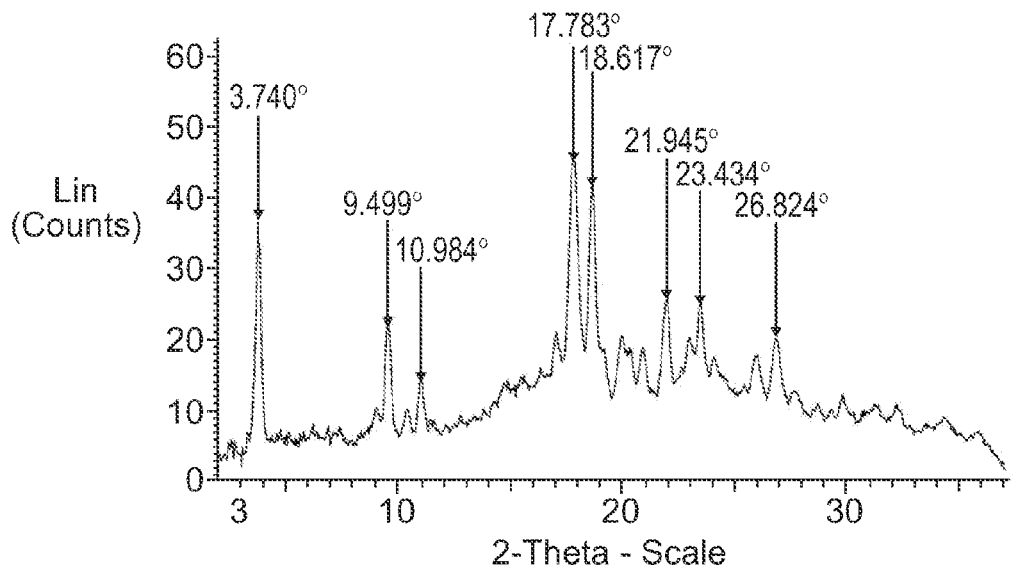
FIG. 2 illustrates a representative peak-picked pXRD spectrum for the crystalline L-proline co-crystal of the compound of formula (I-X).

In another embodiment of the present invention, the crystalline L-proline co-crystal of the compound of formula (I-X) may be characterized by the following pXRD peaks °2θ: 3.74, 9.50, 10.98, 17.78, 18.62, 21.94, 23.43 and 26.82; as shown in the peak-picked pXRD spectrum illustrated in FIG. 2.

The crystalline L-proline co-crystal of the compound of formula (I-X) was further characterized using Differential Scanning Calorimetry (DSC), measuring from 25° C. to 300° C. at 10° C./min and found to exhibit a sharp melting point at 188° C., with a shoulder at 180° C.

The crystalline L-proline co-crystal of the compound of formula (I-X) was further characterized using Thermogravimetric Analysis (TGA), measuring from 25° C. to 300° C. at 10° C./min and found to exhibit weight loss of 1% up to 180° C. (believed to be due to the loss of residual solvent), followed by a further 25% weight loss up to 280° C., corresponding to the loss of 1 mole equivalent of L-proline.

The crystalline L-proline co-crystal of the compound of formula (I-X) was further characterized using Dynamic Vapor Sorption (DVS), measuring from 0% RH to 90% RH (2 full cycles) at 25° C. The crystalline L-proline co-crystal of the compound of formula (I-X) was found to be hygroscopic, although no weight gain was observed until the % RH had reached 40%. Between 40% RH and 90% RH, the co-crystal gained 12% in mass, which was lost (with some hysteresis) during the desorption part of the measurement cycle. pXRD collected after the DVS run (isolated at 0% RH) indicated that no irreversible form conversion was observed with this sample.

Crystalline Citric Acid Co-Crystal Properties:

The crystalline citric acid co-crystal of the compound of formula (I-X) was characterized by powder X-ray diffraction (pXRD) patterns; comparing the co-crystal patterns with the pXRD patterns of the co-crystal components, more particularly the pXRD of the compound of formula (I-X) and the pXRD of the citric acid.

Figure 3:
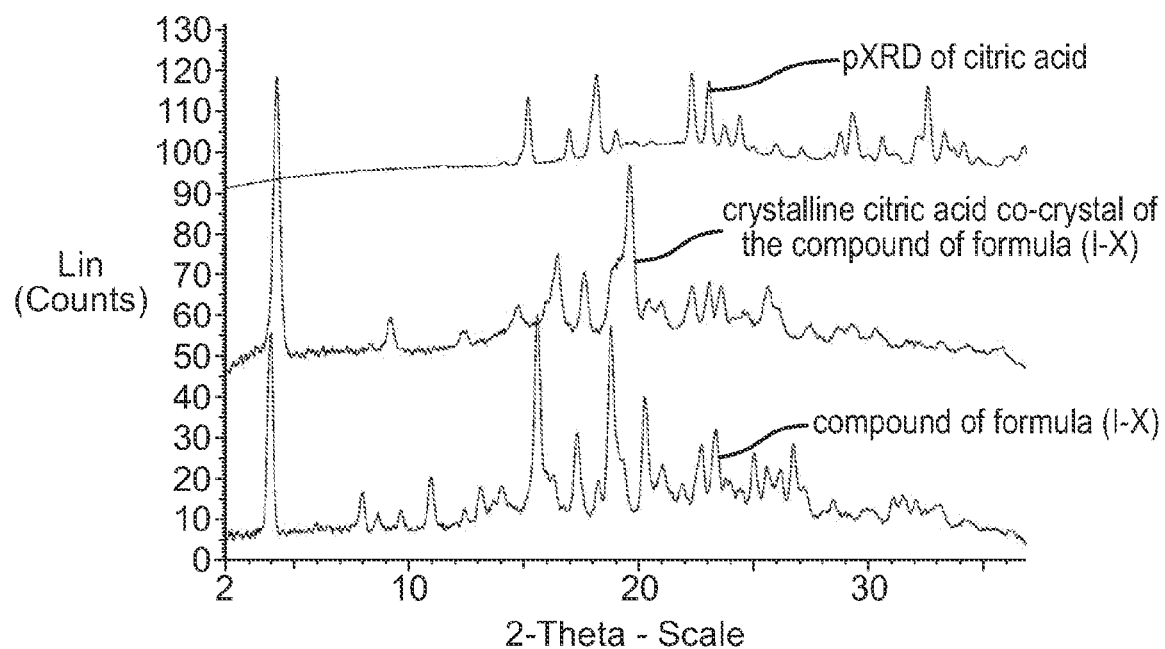
FIG. 3 illustrates a representative pXRD spectrum of citric acid (top), the compound of formula (I-X) (bottom) and the crystalline citric acid co-crystal of the compound of formula (I-X) (middle).

FIG. 3 which follows herein, illustrates representative measured pXRD patterns for citric acid (top), the compound of formula (I-X) (bottom) and the crystalline citric acid co-crystal of the compound of formula (I-X) (middle).

In an embodiment, the crystalline citric acid co-crystal of the compound of formula (I-X) may be characterized by its powder X-ray diffraction pattern, comprising the peaks as listed in Table 2, below.

TABLE 2

Crystalline Citric Acid Co-Crystal of Compound of Formula (I-X)

| No. | Position [°2θ] | d-spacing [Å] | Relative Intensity [%] |
|---|---|---|---|
| 1 | 4.23 | 20.88 | 100 |
| 2 | 9.15 | 9.67 | 7 |
| 3 | 12.40 | 7.14 | 5 |
| 4 | 14.72 | 6.02 | 4 |
| 5 | 16.51 | 5.37 | 24 |
| 6 | 17.68 | 5.02 | 8 |
| 7 | 18.94 | 4.69 | 8 |
| 8 | 19.70 | 4.51 | 43 |
| 9 | 20.65 | 4.31 | 7 |
| 10 | 22.36 | 3.97 | 6 |
| 11 | 23.09 | 3.85 | 8 |
| 12 | 23.63 | 3.76 | 10 |
| 13 | 25.65 | 3.47 | 9 |

Preferably, the crystalline citric acid co-crystal of the compound of formula (I-X) is characterized by its pXRD pattern which comprises peaks having a relative intensity greater than or equal to about 5%, more preferably having a relative intensity greater than or equal to about 10%.

Figure 4:
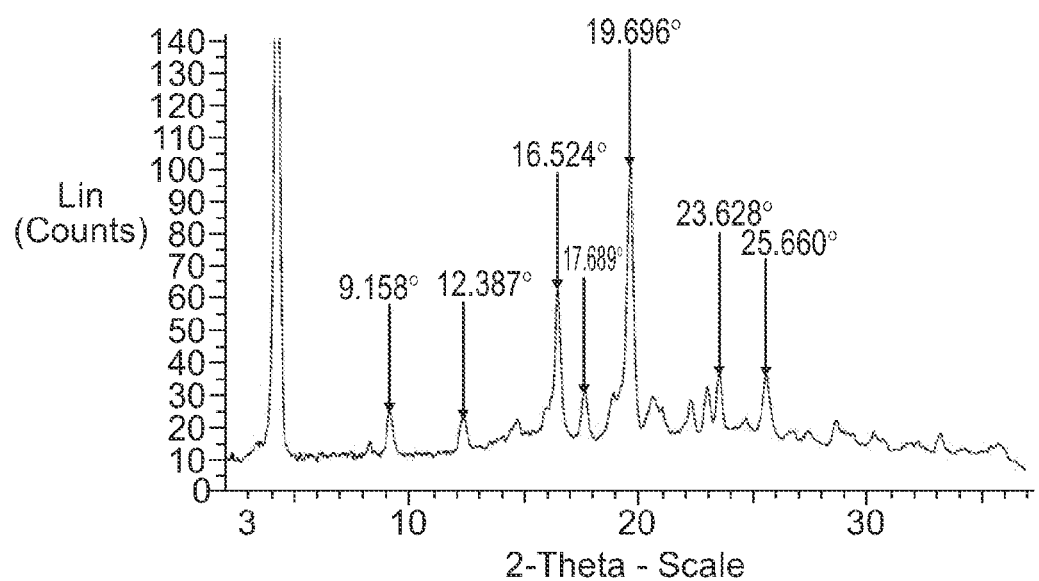
FIG. 4 illustrates a representative peak-picked pXRD spectrum for the crystalline citric acid co-crystal of the compound of formula (I-X).
Figure 5:
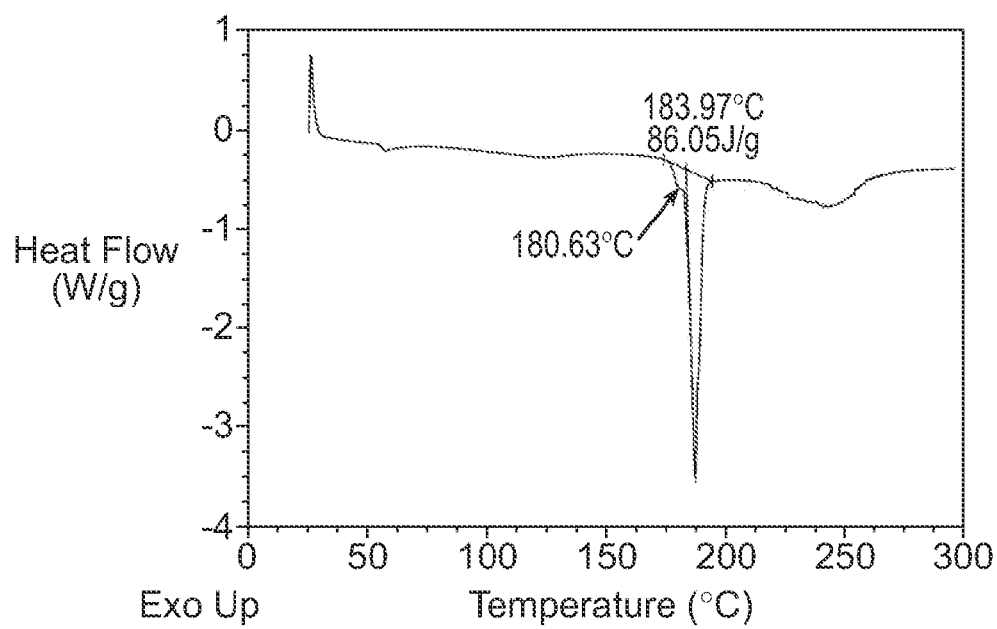
FIG. 5 illustrates a representative DSC scan for the crystalline L-proline co-crystal of the compound of formula (I-X).
Figure 6:
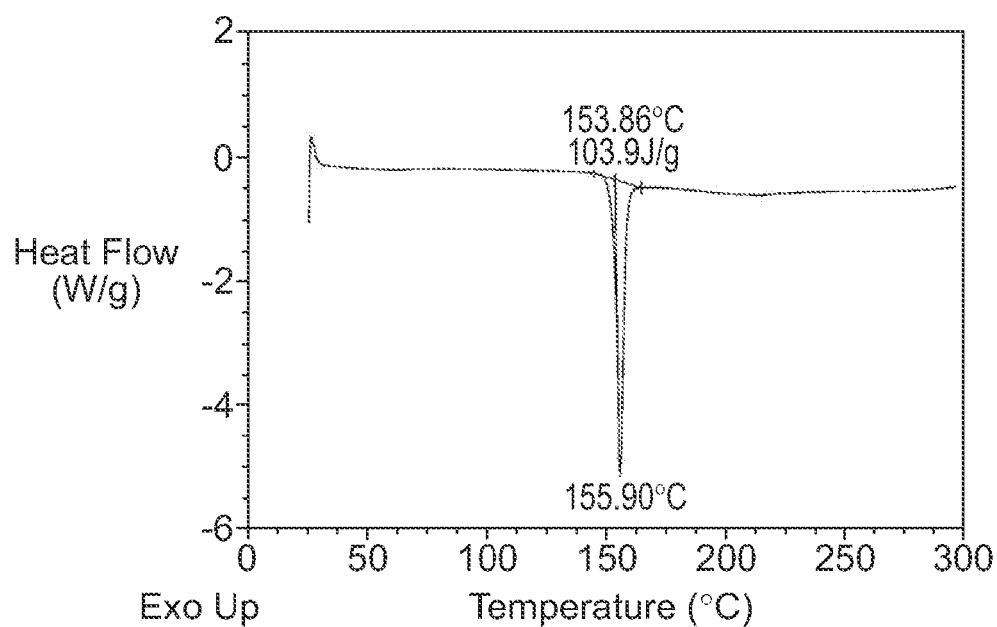
FIG. 6 illustrates a representative DSC scan for the crystalline citric acid co-crystal of the compound of formula (I-X).

In another embodiment of the present invention, the crystalline citric acid co-crystal of the compound of formula (I-X) may be characterized by the following pXRD peaks °2θ: about 4.2, 9.16, 12.39, 16.54, 17.69, 19.70, 23.63 and 25.66; as shown in the peak-picked pXRD spectrum illustrated in FIG. 4.

The crystalline citric acid co-crystal of the compound of formula (I-X) was further characterized using Differential Scanning Calorimetry (DSC), measuring from 25° C. to 300° C. at 10° C./min and found to exhibit a single sharp melting point at 156° C.

The crystalline citric acid co-crystal of the compound of formula (I-X) was further characterized using Thermogravimetric Analysis (TGA), measuring from 25° C. to 300° C. at 10° C./min and found to exhibit insignificant weight loss of 0.38% up to 155° C. This weight loss is believed to be due to the loss of residual solvent and not an indication of the presence of a hydrated form.

The crystalline citric acid co-crystal of the compound of formula (I-X) was further characterized using Dynamic Vapor Sorption (DVS), measuring from 0% RH to 90% RH (2 full cycles) at 25° C. The crystalline citric acid co-crystal of the compound of formula (I-X) was found to be non-hygroscopic, with the gradual increase of 0.5% in mass observed from 0%-80% RH, which mass was lost again on desorption. pXRD collected after the DVS run (isolated at 0% RH) indicated that no form conversion was observed with this sample.

The present invention further comprises pharmaceutical compositions comprising any of the crystalline co-crystals of the compound of formula (I-X), as described herein, with a pharmaceutically acceptable carrier. Pharmaceutical compositions containing one or more of the compounds of the invention described herein as the active ingredient can be prepared by intimately mixing the compound or compounds with a pharmaceutical carrier according to conventional pharmaceutical compounding techniques. The carrier may take a wide variety of forms depending upon the desired route of administration (e.g., oral, parenteral). Thus for liquid oral preparations such as suspensions, elixirs and solutions, suitable carriers and additives include water, glycols, oils, alcohols, flavoring agents, preservatives, stabilizers, coloring agents and the like; for solid oral preparations, such as powders, capsules and tablets, suitable carriers and additives include starches, sugars, diluents, granulating agents, lubricants, binders, disintegrating agents and the like. Solid oral preparations may also be coated with substances such as sugars or be enteric-coated so as to modulate major site of absorption. For parenteral administration, the carrier will usually consist of sterile water and other ingredients may be added to increase solubility or preservation. Injectable suspensions or solutions may also be prepared utilizing aqueous carriers along with appropriate additives.

To prepare the pharmaceutical compositions of this invention, one or more compounds of the present invention as the active ingredient is intimately admixed with a pharmaceutical carrier according to conventional pharmaceutical compounding techniques, which carrier may take a wide variety of forms depending of the form of preparation desired for administration, e.g., oral or parenteral such as intramuscular. In preparing the compositions in oral dosage form, any of the usual pharmaceutical media may be employed. Thus, for liquid oral preparations, such as for example, suspensions, elixirs and solutions, suitable carriers and additives include water, glycols, oils, alcohols, flavoring agents, preservatives, coloring agents and the like; for solid oral preparations such as, for example, powders, capsules, caplets, gelcaps and tablets, suitable carriers and additives include starches, sugars, diluents, granulating agents, lubricants, binders, disintegrating agents and the like. Because of their ease in administration, tablets and capsules represent the most advantageous oral dosage unit form, in which case solid pharmaceutical carriers are obviously employed. If desired, tablets may be sugar coated or enteric coated by standard techniques. For parenterals, the carrier will usually comprise sterile water, through other ingredients, for example, for purposes such as aiding solubility or for preservation, may be included. Injectable suspensions may also be prepared, in which case appropriate liquid carriers, suspending agents and the like may be employed. The pharmaceutical compositions herein will contain, per dosage unit, e.g., tablet, capsule, powder, injection, teaspoonful and the like, an amount of the active ingredient necessary to deliver an effective dose as described above. The pharmaceutical compositions herein will contain, per unit dosage unit, e.g., tablet, capsule, powder, injection, suppository, teaspoonful and the like, of from about 0.1 to about 1000 mg or any amount or range therein, and may be given at a dosage of from about 0.01 to about 500 mg/kg/day, or any amount or range therein, preferably from about 0.5 to about 100 mg/kg/day, or any amount or range therein. The dosages, however, may be varied depending upon the requirement of the patients, the severity of the condition being treated and the compound being employed. The use of either daily administration or post-periodic dosing may be employed.

Preferably these compositions are in unit dosage forms from such as tablets, pills, capsules, powders, granules, sterile parenteral solutions or suspensions, metered aerosol or liquid sprays, drops, ampoules, autoinjector devices or suppositories; for oral parenteral, intranasal, sublingual or rectal administration, or for administration by inhalation or insufflation. Alternatively, the composition may be presented in a form suitable for once-weekly or once-monthly administration; for example, an insoluble salt of the active compound, such as the decanoate salt, may be adapted to provide a depot preparation for intramuscular injection. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a pharmaceutically acceptable salt thereof. When referring to these preformulation compositions as homogeneous, it is meant that the active ingredient is dispersed evenly throughout the composition so that the composition may be readily subdivided into equally effective dosage forms such as tablets, pills and capsules. This solid preformulation composition is then subdivided into unit dosage forms of the type described above containing from 0.01 to about 1,000 mg, or any amount or range therein, of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of material can be used for such enteric layers or coatings, such materials including a number of polymeric acids with such materials as shellac, cetyl alcohol and cellulose acetate.

The liquid forms in which the novel compositions of the present invention may be incorporated for administration orally or by injection include, aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions, include synthetic and natural gums such as tragacanth, acacia, alginate, dextran, sodium carboxymethylcellulose, methylcellulose, polyvinyl-pyrrolidone or gelatin.

The method of treating glucose-related disorders described in the present invention may also be carried out using a pharmaceutical composition comprising any of the compounds as defined herein and a pharmaceutically acceptable carrier. The pharmaceutical composition may contain between about 0.01 mg and about 1000 mg of the compound, or any amount or range therein; preferably about 0.1 mg to about 500 mg of the compound, and may be constituted into any form suitable for the mode of administration selected. Carriers include necessary and inert pharmaceutical excipients, including, but not limited to, binders, suspending agents, lubricants, flavorants, sweeteners, preservatives, dyes, and coatings. Compositions suitable for oral administration include solid forms, such as pills, tablets, caplets, capsules (each including immediate release, timed release and sustained release formulations), granules, and powders, and liquid forms, such as solutions, syrups, elixirs, emulsions, and suspensions. Forms useful for parenteral administration include sterile solutions, emulsions and suspensions.

Advantageously, compounds of the present invention may be administered in a single daily dose, or the total daily dosage may be administered in divided doses of two, three or four times daily. Furthermore, compounds for the present invention can be administered in intranasal form via topical use of suitable intranasal vehicles, or via transdermal skin patches well known to those of ordinary skill in that art. To be administered in the form of a transdermal delivery system, the dosage administration will, of course, be continuous rather than intermittent throughout the dosage regimen.

For instance, for oral administration in the form of a tablet or capsule, the active drug component can be combined with an oral, non-toxic pharmaceutically acceptable inert carrier such as ethanol, glycerol, water and the like. Moreover, when desired or necessary, suitable binders; lubricants, disintegrating agents and coloring agents can also be incorporated into the mixture. Suitable binders include, without limitation, starch, gelatin, natural sugars such as glucose or beta-lactose, corn sweeteners, natural and synthetic gums such as acacia, tragacanth or sodium oleate, sodium stearate, magnesium stearate, sodium benzoate, sodium acetate, sodium chloride and the like. Disintegrators include, without limitation, starch, methyl cellulose, agar, bentonite, xanthan gum and the like.

The liquid forms in suitably flavored suspending or dispersing agents such as the synthetic and natural gums, for example, tragacanth, acacia, methyl-cellulose and the like. For parenteral administration, sterile suspensions and solutions are desired. Isotonic preparations which generally contain suitable preservatives are employed when intravenous administration is desired.

To prepare a pharmaceutical composition of the present invention, a compound of formula (I) as the active ingredient is intimately admixed with a pharmaceutical carrier according to conventional pharmaceutical compounding techniques, which carrier may take a wide variety of forms depending of the form of preparation desired for administration (e.g. oral or parenteral). Suitable pharmaceutically acceptable carriers are well known in the art. Descriptions of some of these pharmaceutically acceptable carriers may be found in *The Handbook of Pharmaceutical Excipients*, published by the American Pharmaceutical Association and the Pharmaceutical Society of Great Britain.

Methods of formulating pharmaceutical compositions have been described in numerous publications such as *Pharmaceutical Dosage Forms: Tablets, Second Edition, Revised and Expanded*, Volumes 1-3, edited by Lieberman et al; *Pharmaceutical Dosage Forms: Parenteral Medications*, Volumes 1-2, edited by Avis et al; and *Pharmaceutical Dosage Forms: Disperse Systems*, Volumes 1-2, edited by Lieberman et al; published by Marcel Dekker, Inc.

The crystalline co-crystals of the compound of formula (I-X) of this invention may be administered in any of the foregoing compositions and according to dosage regimens established in the art whenever treatment of glucose-related is required.

The daily dosage of the products may be varied over a wide range from about 0.01 to about 1,000 mg per adult human per day, or any amount or range therein. For oral administration, the compositions are preferably provided in the form of tablets containing, 0.01, 0.05, 0.1, 0.5, 1.0, 2.5, 5.0, 10.0, 15.0, 25.0, 50.0, 100, 150, 200, 250 and 500 milligrams of the active ingredient for the symptomatic adjustment of the dosage to the patient to be treated.

Preferably, the crystalline co-crystal of the compound of formula (I-X) is administered at a dosage level of from about 0.01 mg/kg to about 500 mg/kg of body weight per day, or 0.01 mg/kg to about 200 mg/kg of body weight per day, or any amount or range therein. Preferably, the range is from about 0.01 to about 50 mg/kg of body weight per day, or any amount or range therein, more preferably, from about 0.05 mg/kg to about 10 mg/kg, or any amount or range therein, more preferably, from about 1 to about 5 mg/kg of body weight per day, or any amount or range therein. In an embodiment, an effective amount of the crystalline co-crystal of the compound of formula (I-X) is supplied at a dosage level of 10 mg, 25 mg, 50 mg, 100 mg, 150 mg or 300 mg, or any amount or range therein. The crystalline co-crystals of the compound of formula (I-X) may be administered on a regimen of 1 to 4 times per day.

Optimal dosages to be administered may be readily determined by those skilled in the art, and will vary with the particular compound used, the mode of administration, the strength of the preparation, the mode of administration, and the advancement of the disease condition. In addition, factors associated with the particular patient being treated, including patient age, weight, diet and time of administration, will result in the need to adjust dosages.

One skilled in the art will recognize that, both in vivo and in vitro trials using suitable, known and generally accepted cell and/or animal models are predictive of the ability of a test compound to treat or prevent a given disorder.

One skilled in the art will further recognize that human clinical trials including first-in-human, dose ranging and efficacy trials, in healthy patients and/or those suffering from a given disorder, may be completed according to methods well known in the clinical and medical arts.

The following Examples are set forth to aid in the understanding of the invention, and are not intended and should not be construed to limit in any way the invention set forth in the claims which follow thereafter.

Example 1

Crystalline L-Proline Co-Crystal of Compound of Formula (I-X)

The compound of formula (I-X) (100 mg) was added to a wig-L-bug vial along with L-proline (26.30 mg) (1:1.1 molar equivalent API:CCF), a grinding ball and acetone (20 μl). The wig-L-bug was subjected to 10 minutes of grinding. After milling the recovered solid was confirmed to be the expected crystalline L-proline co-crystal of the compound of formula (I-X) by pXRD.

Example 2

Crystalline L-Proline Co-Crystal of Compound of Formula (I-X)

The compound of formula (I-X) (50.18 mg) was added to a 4 ml conical vial along with L-proline (13.15 mg) (1:1.1 molar equivalent API:CCF), followed by acetone (2 mL). The capped vial was heated briefly with a heat gun. White solid material precipitated rapidly from the solution and was collected and confirmed to be the expected crystalline L-proline co-crystal of the compound of formula (I-X) by pXRD.

Example 3

Crystalline Citric Acid Co-Crystal of Compound of Formula (I-X)

The compound of formula (I-X) (100 mg) was added to a wig-L-bug vial along with citric acid (43.83 mg) (1:1.1 molar equivalent API:CCF), a grinding ball and isopropyl acetate (20 μl). The wig-L-bug was subjected to 10 minutes of grinding. After milling the recovered solid was confirmed to be the expected crystalline citric acid co-crystal of the compound of formula (I-X) by pXRD.

Example 4

Crystalline Citric Acid Co-Crystal of Compound of Formula (I-X)

The compound of formula (I-X) (50.72 mg) was added to a 4 ml conical vial along with citric acid (21.83 mg) (1:1.1 molar equivalent API:CCF), followed by isopropyl acetate (1 mL). The capped vial was heated with heat gun to completely dissolve the solid materials. As no crystallization was observed on cooling, the cap was opened and the solvent allowed to evaporate slowly. After 2 days (after approximately 20% solvent reduction) seeds of the desired material were added to the saturated solution and a white solid crystalline material precipitated within a few hours. The isolated material was confirmed to be the expected crystalline citric acid co-crystal of the compound of formula (I-X) by pXRD.

Example 5

Solid, Oral Dosage Form—Prophetic Example

As a specific embodiment of an oral composition, 100 mg of the crystalline L-proline co-crystal of the compound of formula (I-X), prepared as described herein is formulated with sufficient finely divided lactose to provide a total amount of 580 to 590 mg to fill a size O hard gel capsule.

Example 6

Solid Oral Dosage Form—Prophetic Example

As a specific embodiment of an oral composition, 100 mg of the crystalline citric acid co-crystal of the compound of formula (I-X), prepared as described herein is formulated with sufficient finely divided lactose to provide a total amount of 580 to 590 mg to fill a size O hard gel capsule.

While the foregoing specification teaches the principles of the present invention, with examples provided for the purpose of illustration, it will be understood that the practice of the invention encompasses all of the usual variations, adaptations and/or modifications as come within the scope of the following claims and their equivalents.

What is claimed:
1. An L-proline co-crystal of a compound of formula (I-X)

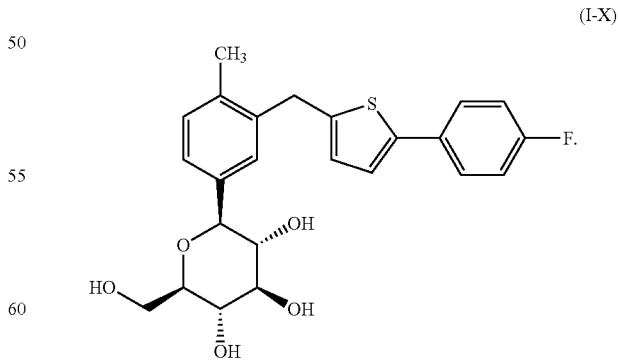

2. The L-proline co-crystal as in claim 1, comprising the following pXRD peaks °2θ: 3.74, 9.50, 10.98, 17.78, 18.62, 21.94, 23.43 and 26.82; wherein the pXRD peaks are measured using Cu/$K_g$ λ1.54056Å radiation.

3. The L-proline co-crystal as in claim 1, wherein the co-crystal exhibits a melting point of 188° C., as measured by DSC.

4. A citric acid co-crystal of a compound of formula (I-X)

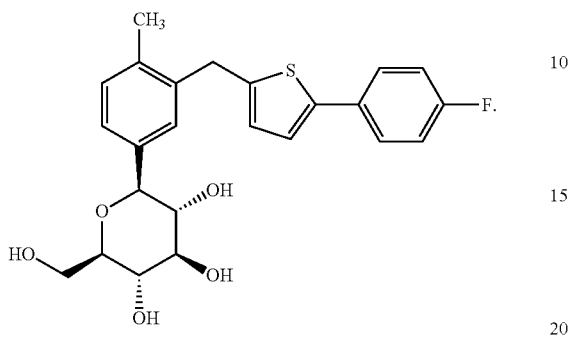

(I-X)

5. The citric acid co-crystal as in claim 4, comprising the following pXRD peaks °2θ: 4.2, 9.16, 12.39, 16.54, 17.69, 19.70, 23.63 and 25.66 wherein the pXRD peaks are measured using Cu/K$_\alpha$λ1.54056Å radiation.

6. The citric acid co-crystal as in claim 4, wherein the co-crystal exhibits a melting point of about 156° C., as measured by DSC.

* * * * *